US012582723B2

(12) United States Patent
Richard et al.

(10) Patent No.: US 12,582,723 B2
(45) Date of Patent: Mar. 24, 2026

(54) POLYNUCLEOTIDES ENCODING A HUMAN FKRP PROTEIN

(71) Applicants: GENETHON, Evry-Courcouronnes (FR); UNIVERSITE D'EVRY-VAL-D'ESSONNE, Evry-Courcouronnes (FR); INSERM (INSTITUT NATIONAL DE LA SANTE ET DE LA RECHERCHE MEDICALE), Paris (FR)

(72) Inventors: Isabelle Richard, Corbeil-Essonnes (FR); Evelyne Gicquel-Zouida, Vert-le-Petit (FR); William Lostal, Savigny sur Orge (FR)

(73) Assignees: GENETHON, Evry Courcouronnes (FR); UNIVERSITE D'EVRY-VAL-D'ESSONNE, Evry Courcouronnes (FR); Inserm (Institut National De La Sante Et De La Recherche Medicale), Paris (FR)

( * ) Notice: Subject to any disclaimer, the term of this patent is extended or adjusted under 35 U.S.C. 154(b) by 277 days.

(21) Appl. No.: 18/177,446

(22) Filed: Mar. 2, 2023

(65) Prior Publication Data

US 2023/0321277 A1        Oct. 12, 2023

Related U.S. Application Data

(63) Continuation of application No. 16/628,650, filed as application No. PCT/EP2018/068420 on Jul. 6, 2018, now Pat. No. 11,596,698.

(30) Foreign Application Priority Data

Jul. 7, 2017    (EP) ..................................... 17305894

(51) Int. Cl.
| | |
|---|---|
| *A61K 31/7088* | (2006.01) |
| *A61K 48/00* | (2006.01) |
| *A61P 21/00* | (2006.01) |
| *C07K 14/47* | (2006.01) |
| *C12N 15/86* | (2006.01) |
| *A61K 38/00* | (2006.01) |

(52) U.S. Cl.
CPC ............ *A61K 48/005* (2013.01); *A61P 21/00* (2018.01); *C07K 14/4707* (2013.01); *C12N 15/86* (2013.01); *A61K 38/00* (2013.01)

(58) Field of Classification Search
CPC .............. C12N 15/102; C12N 2800/22; C12N 2840/105; A61K 47/549; A61K 48/0091; A61K 48/005; A61K 31/7088
See application file for complete search history.

(56) References Cited

U.S. PATENT DOCUMENTS

| | | | |
|---|---|---|---|
| 6,156,303 | A | 12/2000 | Russell et al. |
| 7,282,199 | B2 | 10/2007 | Gao et al. |
| 2017/0368199 | A1 | 12/2017 | Lu et al. |

FOREIGN PATENT DOCUMENTS

| WO | WO 2003/042397 A2 | 5/2003 |
|---|---|---|
| WO | WO 2005/033321 A2 | 4/2005 |
| WO | WO 2016/138387 A1 | 9/2016 |

OTHER PUBLICATIONS

Apparailly et al., "Adeno-associated virus pseudotype 5 vector improves gene transfer in arthritic joints", Hum Gene Ther. Apr. 2005; 16(4):426-34.
Bartoli et al., "Noninvasive monitoring of therapeutic gene transfer in animal models of muscular dystrophies", Gene Ther. Jan. 2006; 13(1):20-8.
Beedle et al., "Mouse fukutin deletion impairs dystroglycan processing and recapitulates muscular dystrophy", J Clin Invest. Sep. 2012;122(9):3330-42.
Beltran-Valero De Bernabe et al., "Mutations in the FKRP gene can cause muscle-eye-brain disease and Walker-Warburg syndrome", J Med Genet 2004;41:e61 (http://www.jmedgenet.com/cgi/content/full/41/5/e61). doi: 10.1136/jmg.2003.013870.
Breton et al., "Structure/function studies of glycosyltransferases", Curr Opin Struct Biol. Oct. 1999;9(5):563-71.
Brockington et al., "Mutations in the fukutin-related protein gene (FKRP) cause a form of congenital muscular dystrophy with secondary laminin alpha2 deficiency and abnormal glycosylation of alpha-dystroglycan", Am J Hum Genet. Dec. 2001;69(6):1198-209.
Fan et al., "Safety and feasibility of high-pressure transvenous limb perfusion with 0.9% saline in human muscular dystrophy", Mol Ther. Feb. 2012;20(2):456-61.
Gicquel et al., "AAV-mediated transfer ofFKRP shows therapeutic efficacy in a murine model but requires control of gene expression", Hum Mol Genet. May 15, 2017;26(10):1952-1965.
Kanagawa et al., "Identification of a Post-translational Modification with Ribitol-Phosphate and Its Defect in Muscular Dystrophy", Cell Rep. Mar. 8, 2016;14(9):2209-2223.
Mercuri et al., "Phenotypic spectrum associated with mutations in the fukutinrelated protein gene", Ann Neurol. Apr. 2003;53(4):537-42.
Muller et al., "Dilated cardiomyopathy may be an early sign of the C826A Fukutinrelated protein mutation", Neuromuscul Disord. May 2005;15(5):372-6.

(Continued)

*Primary Examiner* — Dana H Shin
(74) *Attorney, Agent, or Firm* — KNOBBE, MARTENS, OLSON & BEAR, LLP

(57)        ABSTRACT

The present invention concerns synthetic polynucleotides encoding a human fukutin-related protein (FKRP) wherein the synthetic polynucleotides contain at least a mutation avoiding supplementary transcript(s) generated from frame-shift start codon(s). The synthetic polynucleotides are useful, especially for treating a pathology linked to a FKRP deficiency or induced by a defect in α-dystroglycan (α-DG) glycosylation, such as LGMD2I.

9 Claims, 4 Drawing Sheets

Specification includes a Sequence Listing.

(56)              References Cited

OTHER PUBLICATIONS

Qiao et al., "Muscle and Heart Function Restoration in a Limb Girdle Muscular Dystrophy 21 (LGMD2I) Mouse Model by Systemic FKRP Gene Delivery", Molecular Therapy, vol. 22, No. 11, Nov. 2014.

Rohr et al., "Fast and reliable titration of recombinant adeno-associated virus type-2 using quantitative real-time PCR", Virol Methods. Oct. 2002; 106(1):81-8.

Sharp et al., "Codon usage patterns in *Escherichia coli*, Bacillus subtilis, *Saccharomyces cerevisiae*, Schizosaccharomyces pombe, *Drosophila melanogaster* and *Homo sapiens*; a review of the considerable within-species diversity", Nucleic Acids Res. Sep. 12, 1988;16(17):8207-11.

Sveen et al., "High prevalence and phenotype-genotype correlations of limb girdle muscular dystrophy type 21 in Denmark", Ann Neurol. May 2006;59(5):808-15.

Toromanoff et al., "Safety and Efficacy of Regional Intravenous (RI) Versus Intramuscular (IM) Delivery of rAAV1 and rAAV8 to Nonhuman Primate Skeletal Muscle", Mol Ther. Jul. 2008; 16(7):1291-1299.

Vannoy et al., "Efficacy of Gene Therapy Is Dependent on Disease Progression in Dystrophic Mice with Mutations in the FKRP Gene", Molecular Therapy: Methods & Clinical Development vol. 5, Jun. 16, 2017.

Wahbi et al., "Cardiac assessment of limb-girdle muscular dystrophy 21 patients: an echography, Holter ECG and magnetic resonance imaging study", Neuromuscul Disord. Aug. 2008; 18(8):650-5.

Xu, et al., "Adeno-associated Virus 9 Mediated FKRP Gene Therapy Restores Functional Glycosylation of alpha-Dystroglycan and Improves Muscle Functions", Molecular Therapy, vol. 21, No. 10, Oct. 2013.

International Search Report issued in application No. PCT/EP2018/068420, dated Jul. 25, 2018.

A/

B/

C/

SEQUENCE LISTING

```
Sequence total quantity: 21
SEQ ID NO: 1          moltype = AA  length = 495
FEATURE               Location/Qualifiers
REGION                1..495
                      note = FKRP
source                1..495
                      mol_type = protein
                      organism = Homo sapiens
SEQUENCE: 1
MRLTRCQAAL AAAITLNLLV LFYVSWLQHQ PRNSRARGPR RASAAGPRVT VLVREFEAFD   60
NAVPELVDSF LQQDPAQPVV VAADTLPYPP LALPRIPNVR LALLQPALDR PAAASRPETY  120
VATEFVALVP DGARAEAPGL LERMVEALRA GSARLVAAPV ATANPARCLA LNVSLREWTA  180
RYGAAPAAPR CDALDGDAVV LLRARDLFNL SAPLARPVGT SLFLQTALRG WAVQLLDLTF  240
AAARQPPLAT AHARWKAERE GRARRAALLR ALGIRLVSWE GGRLEWFGCN KETTRCFGTV  300
VGDTPAYLYE ERWTPPCCLR ALRETARYVV GVLEAAGVRY WLEGGSLLGA ARHGDIIPWD  360
YDVDLGIYLE DVGNCEQLRG AEAGSVVDER GFVWEKAVEG DFFRVQYSES NHLHVDLWPF  420
```

```
YPRNGVMTKD TWLDHRQDVE FPEHFLQPLV PLPFAGFVAQ APNNYRRFLE LKFGPGVIEN  480
PQYPNPALLS LTGSG                                                   495

SEQ ID NO: 2           moltype = DNA  length = 1488
FEATURE                Location/Qualifiers
misc_feature           1..1488
                       note = FKRP wt
source                 1..1488
                       mol_type = other DNA
                       organism = Homo sapiens
SEQUENCE: 2
atgcggctca cccgctgcca ggctgccctg gcggccgcca tcaccctcaa ccttctggtc  60
ctcttctatg tctcgtggct gcagcaccag cctaggaatt cccgggcccg ggggcccgt  120
cgtgcctctg ctgccggccc ccgtgtcacc gtcctggtgc gggagttcga ggcatttgac  180
aacgcggtgc ccgagctggt agactccttc ctgcagcaag acccagccca gcccgtggtg  240
gtggcagccg acacgctccc ctacccgccc ctggccctgc cccgcatccc caacgtgcgt  300
ctggcgctgc tccagcccgc cctggaccgg ccagccgcag cctcgcgccc ggagacctac  360
gtggccaccg agtttgtggc cctagtacct gatggggcgc gggctgaggc acctggcctg  420
ctggagcgca tggtggaggc gctccgcgca ggaagcgcac gtctggtggc cgccccggtt  480
gccacggcca accctgccag gtgcctggcc ctgaacgtca gcctgcgaga gtggaccgcc  540
cgctatggcg cagcccccgc cgcgccccgc tgcgacgccc tggacggaga tgctgtggtg  600
ctcctgcgcg cccgcgacct cttcaacctc tcggcgcccc tggcccggcc ggtgggcacc  660
agcctctttc tgcagaccgc ccttcgcggc tgggcggtgc agctgctgga cttgaccttc  720
gccgcggcgc gccagccccc gctggccacg gcccacgcgc gctggaaggc tgagcgcgag  780
ggacgcgctc ggcgggcggc gctgctccgc gcgctgggca tccgcctagt gagctgggaa  840
ggcgggcggc tggagtggtt cggctgcaac aaggagacca cgcgctgctt cggaaccgtg  900
gtgggcgaca cgcccgccta cctctacgag gagcgctgga cgcccccctg ctgcctgcgc  960
gcgctgcgcg agaccgcccg ctatgtggtg ggcgtgctgg aggctgcggg cgtgcgctac  1020
tggctcgagg cggctcact gctggggggcc gcccgccacg gggacatcat cccatgggac  1080
tacgacgtgg acctgggcat ctacttggag gacgtgggca actgcgagca gctgcggggg  1140
gcagaggccg gctcggtggt ggatgagcgc ggcttcgtat gggagaaggc ggtcgagggc  1200
gactttttcc gcgtgcagta cagcgaaagc aaccacttgc acgtggacct gtggcccttc  1260
tacccccgca atggcgtcat gaccaaggac acgtggctgg accaccggca ggatgtggag  1320
tttcccgagc acttcctgca gccgctggtg cccctgcccc ttgccggctt cgtggcgcag  1380
gcgcctaaca actaccgccg cttcctggag ctcaagttcg ggcccggggt catcgagaac  1440
ccccagtacc ccaacccggc actgctgagt ctgacgggaa gcggctga              1488

SEQ ID NO: 3           moltype = DNA  length = 1488
FEATURE                Location/Qualifiers
misc_feature           1..1488
                       note = Synthetic Polynucleotide
misc_feature           1..1488
                       note = "FKRP-OPTmin"
source                 1..1488
                       mol_type = other DNA
                       organism = synthetic construct
SEQUENCE: 3
atgcggctca cccgctgcca ggctgccctg gcggccgcca tcaccctcaa ccttctggtc  60
ctcttctatg tctcgtggct gcagcaccag cctaggaatt cccgggcccg ggggcccgt  120
cgtgcctctg ctgccggccc ccgtgtcacc gtcctggtgc gggagttcga ggcatttgac  180
aacgcggtgc ccgagctggt agactccttc ctgcagcaag acccagccca gcccgtggtg  240
gtggcagccg acacgctccc ctacccgccc ctggccctgc cccgcatccc caacgtgcgt  300
ctggcgctgc tccagcccgc cctggaccgg ccagccgcag cctcgcgccc ggagacctac  360
gtggccaccg agtttgtggc cctagtacct gatggggcgc gggctgaggc acctggcctg  420
ctggagcgga tggtggaggc gctccgcgca ggaagcgca gtctggtggc cgccccggtt  480
gccacggcca accctgccag gtgcctggcc ctgaacgtca gcctgcgaga gtggaccgcc  540
cgctacggcg cagcccccgc cgcgccccgc tgcgacgccc tggacggaga tgctgtggtg  600
ctcctgcgcg cccgcgacct cttcaacctc tcggcgcccc tggcccggcc ggtgggcacc  660
agcctctttc tgcagaccgc ccttcgcggc tgggcggtgc agctgctgga cttgaccttc  720
gccgcggcgc gccagccccc gctggccacg gcccacgcgc gctggaaggc tgagcgcgag  780
ggacgcgctc ggcgggcggc gctgctccgc gcgctgggaa tccgcctagt gagctgggaa  840
ggcgggcggc tggagtggtt cggctgcaac aaggagacca cgcgctgctt cggaaccgtg  900
gtgggcgaca cgcccgccta cctctacgag gagcgctgga cgcccccctg ctgcctgcgc  960
gcgctgcgcg agaccgcccg ctatgtggtg ggcgtgctgg aggctgcggg cgtgcgctac  1020
tggctcgagg cggctcact gctggggggcc gcccgccacg gggacatcat cccatgggac  1080
tacgacgtgg acctgggcat ctacttggag gacgtgggca actgcgagca gctgcggggg  1140
gcagaggccg gctcggtggt ggatgagcgc ggcttcgtat gggagaaggc ggtcgagggc  1200
gactttttcc gcgtgcagta cagcgaaagc aaccacttgc acgtggacct gtggcccttc  1260
tacccccgca atggcgtcat gaccaaggac acgtggctgg accaccggca ggatgtggag  1320
tttcccgagc acttcctgca gccgctggtg cccctgcccc ttgccggctt cgtggcgcag  1380
gcgcctaaca actaccgccg cttcctggag ctcaagttcg ggcccggggt gatcgagaac  1440
ccccagtacc ccaacccggc actgctgagt ctgacgggaa gcggctga              1488

SEQ ID NO: 4           moltype = DNA  length = 1488
FEATURE                Location/Qualifiers
misc_feature           1..1488
                       note = Synthetic Polynucleotide
misc_feature           1..1488
                       note = "FKRP-OPTcomp"
```

```
source                 1..1488
                       mol_type = other DNA
                       organism = synthetic construct
SEQUENCE: 4
atgagactga ccaggtgcca ggctgccctg gctgctgcca tcaccctgaa cctgctggtg   60
ctgttctatg tgagctggct gcagcaccag cccaggaaca gcagggccag gggccccagg  120
agggcctctg ctgctggccc cagggtgaca gtgctggtga gggagtttga ggcctttgac  180
aatgctgtgc ctgagctggt ggacagcttc ctgcagcagg accctgccca gcctgtggtg  240
gtggctgctg ataccctgcc ctaccccccc ctggccctgc ccaggatccc caatgtgagg  300
ctggccctgc tgcagcctgc cctggacagg cctgctgctg ccagcaggcc tgagacctat  360
gtggccacag agtttgtggc cctggtgcct gatgggggcca gggctgaggc ccctggcctg  420
ctggagagga tggtggaggc cctgagggct ggctctgcca ggctggtggc tgcccctgtg  480
gccacagcca accctgccag gtgcctggcc ctgaatgtga gcctgagaga gtggacagcc  540
aggtatgggg ctgcccctgc tgcccccagg tgtgatgccc tggatggaga tgctgtggtg  600
ctgctgaggg ccagggacct gttcaacctg tctgccccccc tggccaggcc tgtggggacc  660
agcctgtttc tgcagacagc cctgaggggc tgggctgtgc agctgctgga cctgaccttt  720
gctgctgcca ggcagcccccc cctggctaca gcccacgcca ggtggaaggc tgagagggag  780
ggcagggcca ggagggctgc cctgcctgagg gccctgggga tcaggctgga gactgggag   840
gggggcaggc tggagtggtt tggctgcaac aaggagacaa ccaggtgctt gggacagtg   900
gtgggggata cccctgccta cctgtatgag gagaggtgga cccccccctg ctgcctgagg   960
gccctgaggg agacagccag gtatgtggtg ggggtgctgg aggctgctgg ggtgaggtac  1020
tggctgagg ggggcagcct gctggggct gccaggcacg gggacattat ccctgggac   1080
tatgatgtgg acctgggcat ctacctggag gatgtgggca actgtgagca gctgaggggg  1140
gctgaggctg ctctgtggt ggatgagagg ggctttgtgt gggagaaggc tgtgaggggg  1200
gactttttca gggtgcagta ctctgagagc aaccacctgc acgtggacct gtggcccttc  1260
taccccagga atggggtgat gaccaaggac acctggctgg accacaggca ggatgtggag  1320
ttccctgagc acttcctgca gcccctggtg cccctgccct ttgctggctt tgtggccag   1380
gcccccaaca actacaggag gttcctggag ctgaagtttg gccctggggt gattgagaac  1440
ccccagtacc ccaaccctgc cctgctgagc ctgacaggct ctggctga            1488
```

```
SEQ ID NO: 5           moltype = DNA  length = 1488
FEATURE                Location/Qualifiers
misc_feature           1..1488
                       note = Synthetic Polynucleotide
misc_feature           1..1488
                       note = "FKRP-OPT-07"
source                 1..1488
                       mol_type = other DNA
                       organism = synthetic construct
SEQUENCE: 5
atgcggctca cccgctgcca ggctgccctg gctgccgcca tcaccctcaa ccttctggtc   60
ctcttctatg tcagctggct gcagcaccag cctaggaatt cccgggcccg ggggcccagg  120
agggcctctg ctgccggccc cagggtcacc gtcctggtgc gggagttcga ggcatttgac  180
aacgctgtgc ccgagctggt agactccttc ctgcagcaag acccagccca gcccgtggtc  240
gtggcagccg acaccctccc ctaccccccc ctggccctgc cccgcatccc caacgtgagg  300
ctggccctgc tccagcccgc cctggaccgg ccagccgcag ccagccgccc tgagacctac  360
gtggccaccg agtttgtggc cctggtacct gatgggggcc gggctgaggc acctggcctg  420
ctggagcgga tggtggaggc cctccgcgca ggaagcgcaa ggctggtggc cgcccctgtt  480
gccacagcca accctgccag gtgcctggcc ctgaacgtca gcctgcgaga gtggaccgcc  540
cgctacggcg cagccccccg cgcccccccgc tgcgacgccc tggacggaga tgctgtggtg  600
ctcctgcggg cccgcgacct cttcaacctc tctgccccccc tggcccggcc tgtggggcacc  660
agcctctttc tgcagaccgc ccttcgcggc tgggctgtgc agctgctgga cttgaccttc  720
gccgctgccc gccagccccc cctggccaca gcccacgccc gctggaaggc tgagcgcgag  780
ggacgcgctc ggcgggctgc cctgctccgc gccctgggaa tccgcctggt gagctgggaa  840
ggcgggcgc tggagtggtt cggctgcaac aaggagacca cccgctgctt cggaaccgtg   900
gtgggcgaca ccccgcccta cctctacagg agcgcctgga ccccccccctg ctgcctgcgcg  960
gccctgcgcg agaccgcccg ctatgtggtg ggcgtgctgg aggctgctgg cgtgcgctac  1020
tggctcgagg gcggctcact gctgggggcc gcccgccacg gggacatcat cccatgggac  1080
tacgacgtgg acctgggcat ctacttggag gacgtgggca actgcgagca gctgcggggg  1140
gcagaggccg gctctgtggt ggatgagcgc ggcttcgtat gggagaaggc tgtcgagggc  1200
gacttttttcc gcgtgcagta cagcgaaagc aaccacttgc acgtggacct gtggcccttc  1260
taccccgcgca atggcgtcat gaccaaggac acctggctgg accaccggca ggatgtggag  1320
tttcccgagc acttcctgca gcccctggtg cccctgccct tgccggctt cgtggcccag  1380
gcccctaaca actaccgccg cttcctggag ctcaagttcg gcccggggt gatcgagaac  1440
ccccagtacc ccaaccctgc actgctgagt ctgaccggaa gcggctga            1488
```

```
SEQ ID NO: 6           moltype = DNA  length = 1488
FEATURE                Location/Qualifiers
misc_feature           1..1488
                       note = Synthetic Polynucleotide
misc_feature           1..1488
                       note = "FKRP-OPT-08"
source                 1..1488
                       mol_type = other DNA
                       organism = synthetic construct
SEQUENCE: 6
atgcggctca cccgctgcca ggctgccctg gctgctgcca tcaccctcaa ccttctggtc   60
ctcttctatg tcagctggct gcagcaccag cctaggaatt cccgggcccg ggggcccagg  120
agggcctctg ctgctggccc cagggtcacc gtcctggtgc gggagttcga ggcatttgac  180
```

-continued

```
aacgctgtgc ccgagctggt agactccttc ctgcagcaag acccagccca gcccgtggtg  240
gtggcagctg acaccctccc ctaccccccc ctggccctgc cccgcatccc caacgtgagg  300
ctggccctgc tccagcccgc cctggaccgg ccagctgcag ccagccgccc tgagacctac  360
gtggccaccg agtttgtggc cctggtacct gatggggccc gggctgaggc acctggcctg  420
ctggagcgga tggtggaggc cctcagggca ggaagcgcaa ggctggtggc tgcccctgtt  480
gccacagcca accctgccag gtgcctggcc ctgaacgtca gcctgcgaga gtggaccgcc  540
cgctacgggg cagcccccgc tgcccccgc tgcgacgccc tggacggaga tgctgtggtg  600
ctcctgaggg ccagggacct cttcaacctc tctgcccccc tggcccggcc tgtgggcacc  660
agcctctttc tgcagaccgc ccttaggggc tgggctgtgc agctgctgga cttgaccttc  720
gctgctgccc gccagccccc cctggccaca gcccacgccc gctggaaggc tgagagggag  780
ggaagggctc ggcgggctgc cctgctcagg gccctgggaa tccgcctggt gagctgggaa  840
gggggggcggc tggagtggtt cggctgcaac aaggagacca cccgctgctt cggaaccgtg  900
gtgggggaca cccccgccta cctctacgag gagcgctgga cccccccctg ctgcctgagg  960
gccctgaggg agaccgcccg ctatgtggtg ggggtgctgg aggctgctgg ggtgcgctac  1020
tggctcgagg ggggctcact gctgggggct gcccgccacg gggacatcat cccatgggac  1080
tacgacgtgg acctgggcat ctacttggag gacgtgggca actgcgagca gctgcggggg  1140
gcagaggctg gctctgtggt ggatgagagg ggcttcgtat gggagaaggc tgtggagggg  1200
gacttttttca gggtgcagta cagcgaaagc aaccacttgc acgtggacct tggccccttc  1260
taccccgca atggggtcat gaccaaggac acctggctgg accaccggca ggatgtggag  1320
tttcccgagc acttcctgca gcccctggtg ccctgcccct tgctggctt cgtcgtgccag  1380
gccccctaaca actaccgccg cttcctggag ctcaagttcg gcccgggggt gatcgagaac  1440
ccccagtacc ccaaccctgc actgctgagt ctgaccggaa gcggctga  1488
```

SEQ ID NO: 7          moltype = DNA   length = 1488
FEATURE               Location/Qualifiers
misc_feature         1..1488
                     note = Synthetic Polynucleotide
misc_feature         1..1488
                     note = "FKRP-OPT-10"
source               1..1488
                     mol_type = other DNA
                     organism = synthetic construct
SEQUENCE: 7

```
atgagactga caaggtgcca ggctgccctg gctgctgcca tcacactgaa cctgctggtg  60
ctgtttttatg tgagctggct gcagcaccag cctaggaaca gcagggccag gggccctagg  120
agggcctctg ctgctggccc tagggtgaca gtgctggtga gggagtttga ggccttttgac  180
aatgctgtgc ctgagctggt ggacagcttt ctgcagcagg accctgccca gcctgtggtg  240
gtggctgctg atacactgcc ttaccctcct ctggccctgc ctaggatccc taatgtgagg  300
ctggccctgc tgcagcctgc cctggacagg cctgctgctg ccagcaggcc tgagacttat  360
gtggccacag agtttgtggc cctggtgcct gatggggcca gggctgaggc ccctggcctg  420
ctggagagga tggtggaggc cctgagggct ggctctgcca ggctggtggc tgcccctgtg  480
gccacagcca accctgccag gtgcctggcc ctgaatgtga gcctgagaga gtggacagcc  540
aggtatgggg ctgccctgc tgcccctagg tgtgatgccc tggatggaga tgctgtggtg  600
ctgctgaggg ccagggacct gtttaacctg tctgccccctc tggccaggcc tgtggggaca  660
agcctgtttc tgcagacagc cctgagggc tgggctgtgc agctgctgga cctgacattt  720
gctgctgcca ggcagcctcc tctggctaca gcccacgcca ggtggaaggc tgagagggag  780
ggcaggggca ggaggggctgc cctgctgagg gccctgggaa tcaggctggt gagctgggaa  840
gggggcaggc tggagtggtt tggctgcaac aaggagacaa caaggtgctt gggacagtg  900
gtggggggata cacctgccta cctgtatgag gagaggtgga cacctccttg ctgcctgagg  960
gccctgaggg agacagccag gtatgtggtg ggggtgctgg aggctgctgg ggtgaggtac  1020
tggctcgagg ggggcagcct gctggggct gccaggcacg gggacattat cccttgggac  1080
tatgatgtgg acctgggcat ctacctggag gatgtgggca actgtgagca gctgaggggg  1140
gctgaggctg gctctgtggt ggatgagagg ggctttgtgt gggagaaggc tgtggagggg  1200
gacttttttta gggtgcagta ctctgagagc aaccacctgc acgtggacct gtggcctttt  1260
taccctagga atggggtgat gacaaaggac acatggctgg accacaggca ggatgtggag  1320
tttcctgagc actttctgca gcctctggtg cctctgcctt ttgctggctt tgtggcccag  1380
gccccctaaca actacaggag gtttctggag ctgaagtttg gccctggggt gattgagaac  1440
cctcagtacc ctaaccctgc cctgctgagc ctgacaggct ctggctga  1488
```

SEQ ID NO: 8          moltype = DNA   length = 1488
FEATURE               Location/Qualifiers
misc_feature         1..1488
                     note = Synthetic Polynucleotide
misc_feature         1..1488
                     note = "FKRP-OPT-11"
source               1..1488
                     mol_type = other DNA
                     organism = synthetic construct
SEQUENCE: 8

```
atgagactga caaggtgcca ggctgccctg gctgctgcca tcacactgaa cctgctggtg  60
ctgtttttatg tgagctggct gcagcaccag cctagaaaca gcagagccag aggccctaga  120
agagcctctg ctgctggccc tagagtgaca gtgctggtga gagagtttga ggccttttgac  180
aatgctgtgc ctgagctggt ggacagcttt ctgcagcagg accctgccca gcctgtggtg  240
gtggctgctg atacactgcc ttaccctcct ctggccctgc ctagaatccc taatgtgagg  300
ctggccctgc tgcagcctgc cctggacaga cctgctgctg ccagcagacc tgagacttat  360
gtggccacag agtttgtggc cctggtgcct gatggggcca gagctgaggc ccctggcctg  420
ctggagagaa tggtggaggc cctgagagct ggctctgcca gactggtggc tgcccctgtg  480
gccacagcca accctgccag atgcctggcc ctgaatgtga gcctgagaga gtggacagcc  540
agatatgggg ctgccctgc tgcccctaga tgtgatgccc tggatggaga tgctgtggtg  600
```

-continued

```
ctgctgagag ccagagacct gtttaacctg tctgcccctc tggccagacc tgtgggggaca   660
agcctgtttc tgcagacagc cctgagaggc tgggctgtgc agctgctgga cctgacattt   720
gctgctgcca gacagcctcc tctggctaca gcccacgcca gatggaaggc tgagagagag   780
ggcagagcca gaagagctgc cctgctgaga gccctgggga tcaggctggt gagctgggag   840
ggggccaagac tggagtgggt tggctgcaac aaggagacaa caagatgctt tgggacagtg   900
gtgggggata cacctgccta cctgtatgag gagaggtgga cacctccttg ctgcctgaga   960
gccctgagag agacagccag atatgtggtg gggtgctgg aggctgctgg ggtgagatac  1020
tggctggagg ggggcagcct gctgggggct gccagacacg gggacattat cccttgggac  1080
tatgatgtgg acctgggcat ctacctggag gatgtgggca actgtgagca gctgagaggg  1140
gctgaggctg gctctgtggt ggatgagaga ggctttgtgt gggagaaggc tgtggaggg  1200
gacttttta gagtgcagta ctctgagagc aaccacctgc acgtggacct gtggcctttt  1260
tacccctagaa atggggtgat gacaaaggac acatggctgg accacagaca ggatgtggag  1320
tttcctgagc actttctgca gcctctggtg cctctgcctt ttgctggctt tgtggcccag  1380
gcccctaaca actacagaag atttctggag ctgaagtttg gccctgggggt gattgagaac  1440
cctcagtacc ctaaccctgc cctgctgagc ctgacaggct ctggctga             1488

SEQ ID NO: 9             moltype = DNA   length = 6903
FEATURE                  Location/Qualifiers
misc_feature            1..6903
                        note = Synthetic Polynucleotide
misc_feature            1..6903
                        note = "pAAV-hDesmin-hFKRPwt"
source                  1..6903
                        mol_type = other DNA
                        organism = synthetic construct
SEQUENCE: 9
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg   120
ttggcgggtg tcgggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cgagctcggt accttaaacc   420
ggttcctaca tatgggttgc gcaatgcggc cgcagtactg cagaaatagg ccgaaatcgg   480
caaaatccct ttattggcca ctccctctct gcgcgctcgc tcgctcactg aggccgggcg   540
accaaaggtc gcccgacgcc cgggctttgc ccgggcggcc tcagtgagcg agcgagcgcg   600
cagagaggga gtggccaact ccatcactag gggttcctta cccctgccc cccacagctc   660
ctctcctgtg ccttgtttcc cagccatgcg ttctcctcta taaataccccg ctctggtatt   720
tggggttggc agctgttgct gccagggaga tggttgggt gacatgcggc tcctgacaaa   780
acacaaaccc ctggtgtgtg tgggcgtggg tggtgtgagt aggggggatga atcagggagg   840
gggcggggga cccaggggggc aggagccaca caaagtctgt gcgggggtgg gagcgcacat   900
agcaattgga aactgaaagc ttatcagacc ctttctggaa atcagcccac tgtttataaa   960
cttgaggccc caccctcgac agtaccgggg aggaagaggg cctgcactag tccagagggga  1020
aactgaggct cagggctagc tcgcccatag acatacatgg caggcaggct ttggccagga  1080
tccctccgcc tgccaggcgt ctccctgccc tccttcctg cctagagacc cccaccctca  1140
agcctggctg gtctttgcct gagacccaaa cctcttcgac ttcaagagaa tatttaggaa  1200
caaggtggtt tagggccttt cctgggaaca ggccttgaca ctttaagaaa tgacccaaag  1260
tctctccttg accaaaaagg ggaccctcaa actaaaggga agcctctctt ctgctgtctc  1320
ccctgacccc actccccccc accccaggac gaggagataa ccaggctga aagaggcccg  1380
cctgggggct gcagacatgc ttgctgcctg ccctggcgaa ggattggcag gcttgcccgt  1440
cacaggaccc ccgctggctg actcaggggc gcaggcctct tgcgggggag ctggcctccc  1500
cgcccccacg gccacggggcc gccctttcct ggcaggacag cgggatcttg cagctgtcag  1560
gggaggggag gcggggggctg atgtcaggag ggatacaaat agtgccgacg gctgggggcc  1620
ctgtctcccc tcgccgcatc cactctccgg ccggccgcct gcccgccgcc tcctccgtgc  1680
gccgccagc ctcgcccgcg tacacatatt gaccaaatca gggtaatttt gcatttgtaa  1740
ttttaaaaaa tgctttcttc ttttaatata ctttttttgtt tatcttattt ctaatacttt  1800
ccctaatctc tttctttcag ggcaataatg atacaatgta tcatgcctct ttgcaccatt  1860
ctaaagaata acagtgataa tttctgggtt aaggcaatag caatatttct gcatataaat  1920
atttctgcat ataaattgta actgatgtaa gaggtttcat attgctaata gcagctacaa  1980
tccagctacc attctgcttt tattttttgg ttgggataag gctggattat tctgagtcca  2040
agctaggccc ttttgctaat cttgttcata cctcttatct tcctccaca gctcctgggc  2100
aacgtgctgg tctctgtgct ggcccatcac tttggcaaag aattcgccac catgcggctc  2160
acccgctgcc aggctgccct ggcggccgcc atcaccctca accttctggt cctcttctat  2220
gtctcgtggc tgcagcacca gcctaggaat tcccgggggcc cgtgcctcc  2280
gctgccggcc cccgtgtcac cgtcctggtg cgggagttcg aggcatttga caacggcggtg  2340
cccgagctgg tagactcctt cctgcagcaa gacccagccc agcccgtggt ggtggcagcc  2400
gacacgctcc cctacccgcc cctggccctg ccccgcatcc ccaacgtgcg tctggcgctg  2460
ctccagcccg ccctggaccg gccagccgca gcctcgcgc cggagaccta cgtggccacc  2520
gagtttgtgg ccctagtacc tgatggggcg cgggctgagg cacctggcct cctggagccg  2580
atggtggagg cgctccgcgc aggaagcgca cgtctggtgg ccgcccccggt tgccacggcc  2640
aaccctgcca ggtgcctggc cctgaacgtc agcctgcgag agtggaccgc ccgctatggc  2700
gcagccccg ccgcgcccg ctgcgacgcc ctggacggag atgctgtggt gctcctcgcg  2760
gccgcgacc tcttcaacct ctcggcgccc ctggcccggc cggtgggcac cagcctcttt  2820
ctgcagaccg cccttcgcgg ctgggcggta cagctcggt acttgacctt ccgcttcggc  2880
cgccagcccc cgctggccac ggccacgcgc cgctggaagg ctgagcgcga gggacgcgct  2940
cggcgggcgg cgctgctccg cgcgctgggc atccgcctag tgagctggga aggcgggcgg  3000
ctggagtggt cggctgcaa caaggagacc acgcgctgct cggaaccgt ggtgggcgac  3060
acgcccgcct acctctacga ggagcgctgg acgccccct gctgcctgcg cgcgctgcgc  3120
gagaccgccc gctatgtggt gggcgtgctg gaggctgcgg cgtgcgcta ctggctcgag  3180
```

```
ggcggctcac tgctgggggc cgcccgccac ggggacatca tcccatggga ctacgacgtg   3240
gacctgggca tctacttgga ggacgtgggc aactgcgagc agctgcgggg ggcagaggcc   3300
ggctcggtgg tggatgagcg cggcttcgta tgggagaagg cggtcgaggg cgacttttc    3360
cgcgtgcagt acagcgaaag caaccacttg cacgtggacc tgtggccctt ctacccccgc   3420
aatggcgtca tgaccaagga cacgtggctg gaccaccggc aggatgtgga gtttcccgag   3480
cacttcctgc agccgctggt gccctgccc  tttgccggct tcgtggcgca ggcgcctaac   3540
aactaccgcc gcttcctgga gctcaagttc gggcccgggg tcatcgagaa cccccagtac   3600
cccaaccccgg cactgctgag tctgacggga agcggctgaa ttcaccccac cagtgcaggc   3660
tgcctatcag aaagtggtgg ctggtgtggc taatgccctg cccacaagt atcactaagc    3720
tcgctttctt gctgtccaat ttctattaaa ggttcctttg ttccctaagt ccaactacta   3780
aactggggga tattatgaag ggccttgagc atctggattc tgcctaataa aaaacattta   3840
ttttcattgc aatgatgtat ttaaattatt tctgaatatt ttactaaaaa gggaatgtgg   3900
gaggtcagtg catttaaaac ataaagaaat gaagagctag ttcaaacctt gggaaaatac   3960
actatatctt aaactccatg aaagaaggtg aggctgcaaa cgctaatgc acattggcaa     4020
cagccctgat gcctatgcct tattcatccc tcagaaaagg attcaagtag aggcttgatt   4080
tggaggttaa agtttgcta  tgctgtattt tacattactt attgttttag ctgtcctcat    4140
gaatgtcttt tcactaccca tttgcttatc ctgcatctct cagccttgac tccactcagt   4200
tctcttgctt agagatacca cctttcccct gaagtgttcc ttccatgttt tacggcgaga   4260
tggtttctcc tcgcctggcc actcagcctt agttgtctct gttgtcttat agaggtctac    4320
ttgaagaagg aaaaacaggg ggcatggttt gactgtcctg tgagcccttc ttccctgcct   4380
cccccactca cagtgacccg gaatcaggaa cccctagtga tggagttggc cactccctct   4440
ctgcgcgctc gctcgctcac tgaggccggg cgaccaaagg tcgcccgacg cccgggcttt   4500
gcccgggcgg cctcagtgag cgagcgagcg cgcagagagg gagtggccaa tttgagttct   4560
tctactcagg ttaaacttaa gcgcggccgc agtcctaggt tgcgcaatgg gcatgctaca   4620
gatcttccgc ggtgcagcaa gtcgactgca gaggcctgca tgcaagcttg gcgtaatcat   4680
ggtcatagct gtttcctgtg tgaaattgtt atccgctcac aattccacac aacatacgag   4740
ccggaagcat aaagtgtaaa gcctggggtg cctaatgagt gagctaactc acattaattg   4800
cgttgcgctc actgcccgct ttccagtcgg gaaacctgtc gtgccagctg cattaatgaa   4860
tcggccaacg cgcggggaga ggcggtttgc gtattgggcg ctcttccgct tcctcgctca   4920
ctgactcgct gcgctcggtc gttcggctgc ggcgagcggt atcagctcac tcaaaggcgg   4980
taatacggtt atccacagaa tcaggggata acgcaggaaa gaacatgtga gcaaaaggcc   5040
agcaaaaggc caggaaccgt aaaaaggccg cgttgctggc gtttttccat aggctccgcc   5100
cccctgacga gcatcacaaa aatcgacgct caagtcagag gtggcgaaac ccgacaggac   5160
tataaagata ccaggcgttt ccccctggaa gctccctcgt gcgctctcct gttccgaccc   5220
tgccgcttac cggatacctg tccgcctttc tcccttcggg aagcgtggcg ctttctcata   5280
gctcacgctg taggtatctc agttcggtgt aggtcgttcg ctccaagctg ggctgtgtgc   5340
acgaaccccc cgttcagccc gaccgctgcg ccttatccgg taactatcgt cttgagtcca   5400
acccggtaag acacgactta tcgccactgg cagcagccac tggtaacagg attagcagag   5460
cgaggtatgt aggcggtgct acagagttct tgaagtggtg gcctaactac ggctacacta   5520
gaagaacagt atttggtatc tgcgctctgc tgaagccagt taccttcgga aaaagagttg   5580
gtagctcttg atccggcaaa caaaccaccg ctggtagcgg tggtttttt  gtttgcaagc    5640
agcagattac gcgcagaaaa aaaggatctc aagaagatcc tttgatcttt tctacggggt   5700
ctgacgctca gtggaacgaa aactcacgtt aagggatttt ggtcatgaga ttatcaaaaa   5760
ggatcttcac ctagatcctt ttaaattaaa aatgaagttt taaatcaatc taaagtatat   5820
atgagtaaac ttggtctgac agttaccaat gcttaatcag tgaggcacct atctcagcga   5880
tctgtctatt tcgttcatcc atagttgcct gactccccgt cgtgtagata actacgatac    5940
gggagggctt accatctggc cccagtgctg caatgatacc gcgagaccca cgctcaccgg   6000
ctccagattt atcagcaata aaccagccag ccggaagggc cgagcgcaga agtggtcctg   6060
caactttatc cgcctccatc cagtctatta attgttgccg ggaagctaga gtaagtagtt   6120
cgccagttaa tagtttgcgc aacgttgttg ccattgctac aggcatcgtg gtgtcacgct   6180
cgtcgtttgg tatggcttca ttcagctccg gttcccaacg atcaaggcga gttacatgat   6240
cccccatgtt gtgcaaaaaa gcggttagct ccttcggtcc tccgatcgtt gtcagaagta   6300
agttggccgc agtgttatca ctcatggtta tggcagcact gcataattct cttactgtca   6360
tgccatccgt aagatgcttt tctgtgactg gtgagtactc aaccaagtca ttctgagaat   6420
agtgtatgcg gcgaccgagt tgctcttgcc cggcgtcaat acgggataat accgcgccac   6480
atagcagaac tttaaaagtg ctcatcattg gaaaacgttc ttcggggcga aaactctcaa   6540
ggatcttacc gctgttgaga tccagttcga tgtaacccac tcgtgcaccc aactgatctt   6600
cagcatcttt tactttcacc agcgtttctg ggtgagcaaa aacaggaagg caaaatgccg   6660
caaaaaaggg aataagggcg acacggaaat gttgaatact catactcttc cttttttcaat   6720
attattgaag catttatcag ggttattgtc tcatgagcgg atacatattt gaatgtattt   6780
agaaaaataa acaaataggg gttccgcgca catttccccg aaaagtgcca cctgacgtct    6840
aagaaaccat tattatcatg acattaacct ataaaaatag gcgtatcacg aggccctttc   6900
gtc                                                                  6903
```

```
SEQ ID NO: 10           moltype = DNA   length = 6903
FEATURE                 Location/Qualifiers
misc_feature            1..6903
                        note = Synthetic Polynucleotide
misc_feature            1..6903
                        note = "pAAV-hDesmin-hFKRP-OPTmin "
source                  1..6903
                        mol_type = other DNA
                        organism = synthetic construct
SEQUENCE: 10
tcgcgcgttt cggtgatgac ggtgaaaacc tctgacacat gcagctcccg gagacgtca    60
cagcttgtct gtaagcggat gccgggagca gacaagcccg tcaggcgcg tcagcgggtg     120
ttggcgggtg tcgggctgg  cttaactatg cggcatcaga gcagattgta ctgagagtgc   180
accatatgcg gtgtgaaata ccgcacagat gcgtaaggag aaaataccgc atcaggcgcc   240
attgccatt  caggctgcgc aactgttggg aagggcgatc ggtgcgggcc tcttcgctat   300
```

-continued

```
tacgccagct ggcgaaaggg ggatgtgctg caaggcgatt aagttgggta acgccagggt    360
tttcccagtc acgacgttgt aaaacgacgg ccagtgaatt cgagctcggt accttaaacc    420
ggttcctaca tatgggttgc gcaatgcggc cgcagtactg cagaaatagg ccgaaatcgg    480
caaaatccct ttattggcca ctccctctct gcgcgctcgc tcgctcactg aggccgggcg    540
accaaaggtc gcccgacgcc cgggctttgc ccgggcggac tcagtgagcg agcgagcgcg    600
cagagaggga gtggccaact ccatcactag gggttcctta cccctgccc cccacagctc    660
ctctcctgtg ccttgtttcc cagccatgcg ttctcctcta taaatacccg ctctggtatt    720
tggggttggc agctgttgct gccagggaga tggttgggtt gacatgcggc tcctgacaaa    780
acacaaaccc ctggtgtgtg tgggcgtggg tggtgtgagt aggggatga atcagggagg    840
gggcgggga cccaggggc aggagccaca caaagtctgt gcgggggtgg gagcgcacat    900
agcaattgga aactgaaagc ttatcagacc ctttctggaa atcagcccac tgtttataaa    960
cttgaggccc caccctcgac agtaccgggg aggaagaggg cctgcactag tccagaggga   1020
aactgaggct cagggctagc tcgcccatag acatacatgg caggcaggct ttggccagga   1080
tccctccgcc tgccaggcgt ctccctgccc tcccttcctg cctagagacc cccaccctca   1140
agcctggctg gtctttgcct gagacccaaa cctcttcgac ttcaagagaa tatttaggaa   1200
caaggtggtt tagggccttt cctgggaaca ggccttgacc cttaagaaa tgacccaaag   1260
tctctccttg accaaaaagg ggaccctcaa actaaagga agcctctctt ctgctgtctc   1320
ccctgacccc actcccccc accccaggac gaggagataa ccagggctga aagaggcccg   1380
cctgggggct gcagacatgc ttgctgcctg ccctggcgaa ggattggcag gcttgcccgt   1440
cacaggaccc ccgctggctg actcaggggc gcaggcctct tgcggggag ctggcctccc   1500
cgcccccacg gccacgggcc gccctttcct ggcaggacag cgggatcttg cagctgtcag   1560
gggaggggag gcggggctg atgtcaggag ggatacaaat agtgccgacg gctgggggcc   1620
ctgtctcccc tcgccgcatc cactctccgg ccggccgcct gcccgccgcc tcctccgtgc   1680
gcccgccagc ctcgcccgcg tacacatatt gaccaaatca gggtaatttt gcatttgtaa   1740
ttttaaaaaa tgctttcttc ttttaatata cttttttgtt tatcttattt ctaatacttt   1800
ccctaatctc tttctttcag ggcaataatg atacaatgta tcatgcctct ttgcaccatt   1860
ctaaagaata acagtgataa tttctgggtt aaggcaatag caatatttct gcatataaat   1920
atttctgcat ataaattgta actgatgtaa gaggtttcat attgctaata gcagctacaa   1980
tccagctacc attctgcttt tattttttgg ttgggataag gctggattat tctgagtcca   2040
agctaggccc ttttgctaat cttgttcata cctcttatct tcctcccaca gctcctgggc   2100
aacgtgctgg tctctgtgct ggcccatcac tttggcaaag aattcgccac catgcggctc   2160
accgctgcc aggctgccct ggcggccgcc atcaccctca accttctggt cctcttctat   2220
gtctcgtggc tgcagcacca gcctaggaat tcccgggccc ggggcccccg tcgtgcctct   2280
gctgccggcc cccgtgtcac cgtcctggtg cgggagttcg aggcatttga caacgcggtg   2340
cccgagctgg tagactcctt cctgcagcaa gacccagccc agcccgtggt ggtggcagcc   2400
gacacgctcc cctacccgcc cctggccctg ccccgcatcc ccaacgtgcg tctggcgctg   2460
ctccagcccg ccctggaccg gccagccgca gcctcgcgcc cggagaccta cgtggccacc   2520
gagtttgtgg ccctagtacc tgatgggcg cgggctgagg cacctggcct gctggagcgg   2580
atggtggagg cgctccgcgc aggaagcgca cgtctggtgg ccgccccggt tgccacggcc   2640
aaccctgcca ggtgcctggc cctgaacgtc agcctgcgag agtggaccgc ccgctacgcc   2700
gcagccccg ccgcgccccg ctgcgacgcc ctggacggag atgctgtggt gctcctgcgc   2760
gcccgcgacc tcttcaacct ctcggcgccc ctggcccggc cggtgggcac cagcctcttt   2820
ctgcagaccg cccttcgcgg ctgggcggtg cagctgctcc acttgacctt cgccgcggcg   2880
cgccagcccc cgctggccac ggcccacgcg cgctggaagg ctgagcgcga gggacgcgct   2940
cggcgggcgg cgctgctccg cgcgctggga atccgcctag tgagctggga aggcgggcgg   3000
ctggagtggt tcggctgcaa caaggagacc acgcgctgct tcggaaccgt ggtgggcgac   3060
acgccgcct acctctacga ggagcgctgg acgcccccct gctgcctgcg cgcgctgcgc   3120
gagaccgccc gctatgtggt gggcgtgctg gaggctgcgg gcgtgcgcta ctggctcgag   3180
ggcggctcac tgctgggggc cgcccgccac ggggacatca tcccatggga ctacgacgtg   3240
gacctgggca tctacttgga ggacgtgggc aactgcgagc agctgcgggg ggcagaggcc   3300
ggctcggtgg tggatgagcg cggcttcgta tgggagaagg cggtcgaggg cgacttttc   3360
cgcgtgcagt acagcgaaag caaccacttg cacgtggacc tgtggccctt ctacccccga   3420
aatggcgtca tgaccaagga cacgtggctg gaccaccggc aggatgtgga gtttcccgag   3480
cacttcctgc agccgctggt gccctgccc tttgccggct tcgtggcgca ggcgcctaac   3540
aactaccgcc gcttcctgga gctcaagttc gggccgggg tgatcgagaa cccccagtac   3600
cccaacccgg cactgctgag tctgacggga agcggctgaa ttcaccccac cagtgcaggc   3660
tgcctatcag aaagtggtgg ctggtgtggc taatgccctg gcccacaagt atcactaagc   3720
tcgctttctt gctgtccaat ttctattaaa ggttcctttg ttccctaagt ccaactacta   3780
aactggggga tattatgaag ggccttgagc atctggattc tgcctaataa aaaacattta   3840
ttttcattgc aatgatgtat ttaaattatt tctgaatatt ttactaaaaa gggaatgtgg   3900
gaggtcagtg catttaaaac ataaagaaat gaagagctag ttcaaacctt gggaaaatac   3960
actatatctt aaactccatg aaagaaggtg aggctgcaaa cagctaatgc acattggcaa   4020
cagccctgat gcctatgcct tattcatccc tcagaaaagg attcaagtag aggcttgatt   4080
tggaggttaa agttttgcta tgctgtattt tacattactt attgttttag ctgtcctcat   4140
gaatgtcttt tcactaccca tttgcttatc ctgcatctct cagccttgac tccactcagt   4200
tctcttgctt agagatacca cctttccct gaagtgttcc ttccatgttt tacggcgaga   4260
tggtttctcc tcgcctggcc actcagcctt agttgtctct gttgtcttat agaggtctac   4320
ttgaagaagg aaaaacaggg ggcatggttt gactgtcctg tgagcccttc ttccctgcct   4380
cccccactca cagtgacccg gaatccaggaa cccctagttg tggagttggc cactccctct   4440
ctgcgcgctc gctcgctcac tgaggccggg cgaccaaagg tcgcccgacg cccgggcttt   4500
gcccgggcgg cctcagtgag cgagcgagcg cgcagagagg gagtggccaa tttagttct   4560
tctactcagg ttaaacttaa gcgcggccgc agtcctaggt tgcgcaatgg gcatgctaca   4620
gatcttccgc ggtgcagcaa gtcgactgca gaggcctgca tgcaagcttg gcgtaatcat   4680
ggtcatagct gtttcctgtg tgaaattgtt atccgctcac aattccacac aacatacgag   4740
ccggaagcat aaagtgtaaa gcctggggtg cctaatgagt gagctaactc acattaattg   4800
cgttgcgctc actgcccgct ttccagtcgg gaaacctgtc gtgccagctg cattaatgaa   4860
tcggccaacg cgcggggaga ggcggtttgc gtattgggcg ctcttccgct tcctcgctca   4920
ctgactcgct gcgctcggtc gttcggctgc ggcgagcggt atcagctcac tcaaaggcgg   4980
taatacggtt atccacagaa tcaggggata acgcaggaaa gaacatgtga gcaaaaggcc   5040
```

-continued

```
agcaaaaggc caggaaccgt aaaaaggccg cgttgctggc gtttttccat aggctccgcc   5100
cccctgacga gcatcacaaa aatcgacgct caagtcagag gtggcgaaac ccgacaggac   5160
tataaagata ccaggcgttt ccccctggaa gctccctcgt gcgctctcct gttccgaccc   5220
tgccgcttac cggatacctg tccgcctttc tcccttcggg aagcgtggcg ctttctcata   5280
gctcacgctg taggtatctc agttcggtgt aggtcgttcg ctccaagctg ggctgtgtgc   5340
acgaacgccc cgttcagccc gaccgctgcg ccttatccgg taactatcgt cttgagtcca   5400
acccggtaag acacgactta tcgccactgg cagcagccac tggtaacagg attagcagag   5460
cgaggtatgt aggcggtgct acagagttct tgaagtggtg gcctaactac ggctacacta   5520
gaagaacagt atttggtatc tgcgctctgc tgaagccagt taccttcgga aaaagagttg   5580
gtagctcttg atccggcaaa caaaccaccg ctggtagcgg tggtttttt gtttgcaagc   5640
agcagattac gcgcagaaaa aaaggatctc aagaagatcc tttgatcttt tctacggggt   5700
ctgacgctca gtggaacgaa aactcacgtt aagggatttt ggtcatgaga ttatcaaaaa   5760
ggatcttcac ctagatcctt ttaaattaaa aatgaagttt taaatcaatc taaagtatat   5820
atgagtaaac ttggtctgac agttaccaat gcttaatcag tgaggcacct atctcagcga   5880
tctgtctatt tcgttcatcc atagttgcct gactccccgt cgtgtagata actacgatac   5940
gggagggctt accatctggc cccagtgctg caatgatacc gcgagaccca cgctcaccgg   6000
ctccagattt atcagcaata aaccagccag ccggaagggc cgagcgcaga agtggtcctg   6060
caactttatc cgcctccatc cagtctatta ttgttgccgg gaagctaga gtaagtagtt   6120
cgccagttaa tagtttgcgc aacgttgttg ccattgctac aggcatcgtg gtgtcacgct   6180
cgtcgtttgg tatggcttca ttcagctccg gttcccaacg atcaaggcga gttacatgat   6240
cccccatgtt gtgcaaaaaa gcggttagct ccttcggtcc tccgatcgtt gtcagaagta   6300
agttggccgc agtgttatca ctcatggtta tggcagcact gcataattct cttactgtca   6360
tgccatccgt aagatgcttt tctgtgactg gtgagtactc aaccaagtca ttctgagaat   6420
agtgtatgcg gcgaccgagt tgctcttgcc cggcgtcaat acgggataat accgcgccac   6480
atagcagaac tttaaaagtg ctcatcattg gaaaacgttc ttcggggcga aaactctcaa   6540
ggatcttacc gctgttgaga tccagttcga tgtaacccac tcgtgcaccc aactgatctt   6600
cagcatcttt tactttcacc agcgtttctg ggtgagcaaa aacaggaagg caaaatgccg   6660
caaaaaaggg aataagggcg acacggaaat gttgaatact catactcttc ctttttcaat   6720
attattgaag catttatcag ggttattgtc tcatgagcgg atacatattt gaatgtattt   6780
agaaaaataa acaaataggg gttccgcgca catttccccg aaaagtgcca cctgacgtct   6840
aagaaaccat tattatcatg acattaacct ataaaaatag gcgtatcacg aggccctttc   6900
gtc                                                                 6903
```

```
SEQ ID NO: 11          moltype = DNA  length = 6903
FEATURE                Location/Qualifiers
misc_feature           1..6903
                       note = Synthetic Polynucleotide
misc_feature           1..6903
                       note = "pAAV-hDesmin-hFKRP-OPTcomp"
source                 1..6903
                       mol_type = other DNA
                       organism = synthetic construct
SEQUENCE: 11
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg    120
ttggcggggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt accttaaacc    420
ggttcctaca tatgggttgc gcaatgcggc cgcagtactg cagaaatagg ccgaaatcgg    480
caaaatccct ttattggcca ctccctctct gcgcgctcgc tcgctcactg aggccgggcg    540
accaaaggtc gcccgacgcc cgggctttgc ccgggcggcc tcagtgagcg agcgagcgcg    600
cagagaggga gtggccaact ccatcactag gggttcctta cccctgccc cacacagctc    660
ctctcctgtg ccttgtttcc cagccatgcg ttctcctca taaatacccg ctctggtatt    720
tggggttggc agctgttgct gccagggaga tggttgggtt gacatgcggc tcctgacaaa    780
acacaaaccc ctggtgtgtg tgggcgtggg tggtgtgagt aggggatga atcagggagg    840
gggcggggga cccagggggc aggagccaca caaagtctgt gcggggtgg gagcgcacat    900
agcaattgga aactgaaagc ttatcagacc ctttctggaa atcagcccac tgtttataaa    960
cttgaggccc caccctcgac agtaccgggg aggaagaggg cctgcactag tccagaggga   1020
aactgaggct cagggctagc tcgcccatag acatacatgg caggcaggct ttggccagga   1080
tccctccgcc tgccaggcgt ctccctgccc tccttcctg cctagagacc cccaccctca   1140
agcctggctg gtctttgcct gagacccaaa cctcttcgac ttcaagagaa tatttaggaa   1200
caaggtggtt tagggccttt cctgggaaca ggccttgacc ctttaagaaa tgacccaaag   1260
tctctccttg accaaaaagg ggaccctcaa actaaaggga agcctctctt ctgctgtctc   1320
ccctgacccc actcccccc accccaggac gaggagataa ccaggggtga aagaggcccg   1380
cctgggggct gcagacatgc ttgctgcctg ccctggcgaa ggattggcag gcttgccgt   1440
cacaggaccc ccgctggctg actcagggc gcaggcctct tgcggggag ctggcctccc   1500
cgcccccacg gccacgggcc gcccttcct ggcaggacag gggatcttg cagctgtcag   1560
gggagggggag gcgggggctg atgtcaggag ggatacaaat agtgccgacg gctggggggcc   1620
ctgtctcccc tcgccgcatc cactctccgg ccggccgcct gccgccgcc tcctccgtgc   1680
gcccgccagc ctcgcccgcg tacacatatt gaccaaatca gggtaatttt gcatttgtaa   1740
ttttaaaaaa tgctttcttc ttttaatata ctttttttgtt tatcttattt ctaatacttt   1800
ccctaatctc tttctttcag ggcaataatg atacaatgta tcatgcctct ttgcaccatt   1860
ctaaagaata acagtgataa tttctgggtt aaggcaatag caatatttct gcatataaat   1920
atttctgcat ataaattgta actgatgtaa gaggtttcat attgctaata gcagctacaa   1980
tccagctacc attctgcttt tattttttgg ttgggataag ctggattat tctgagtcca   2040
agctaggccc ttttgctaat cttgttcata cctcttatct tcctcccaca gctcctgggc   2100
aacgtgctgg tctctgtgct ggcccatcac tttggcaaag aattcgccac catgagactg   2160
```

```
accaggtgcc aggctgccct ggctgctgcc atcaccctga acctgctggt gctgttctat    2220
gtgagctggc tgcagcacca gcccaggaac agcagggcca ggggccccag gagggcctct    2280
gctgctggcc ccaggtgac agtgctggtg agggagtttg aggcctttga caatgctgtg     2340
cctgagctgg tggacagctt cctgcagcag gaccctgccc agcctgtggt ggtggctgct    2400
gataccctgc cctacccccc cctggccctg cccaggatcc ccaatgtgag gctggccctg    2460
ctgcagcctg ccctggacag gcctgctgct gccagcaggc ctgagaccta tgtggccaca    2520
gagtttgtgg ccctggtgcc tgatggggcc agggctgagg ccctggcct gctggagagg      2580
atggtggagg ccctgagggc tggctctgcc aggctggtgg ctgccctgt ggccacagcc      2640
aaccctgcca ggtgcctggc cctgaatgtg agcctgagag agtggacagc caggtatggg    2700
gctgcccctg ctgcccccag gtgtgatgcc ctggatggag atgctgtggt gctgctgagg    2760
gccagggacc tgttcaacct gtctgccccc ctggccaggc ctgtggggac cagcctgttt    2820
ctgcagacag ccctgagggg ctgggctgtg cagctgctgg acctgacctt tgctgctgcc    2880
aggcagcccc ccctggctac agcccacgcc aggtggaagg ctgagaggga gggcagggcc    2940
aggagggctg ccctgctgag ggccctgggg atcaggctgg tgagctggga gggggcaggg    3000
ctggagtggt ttggctgcaa caaggagaca accaggtgct ttgggacagt ggtgggggat    3060
accccctgcct acctgtatga ggagaggtgg acccccccct gctgcctgag ggccctgagg    3120
gagacagcca ggtatgtggt ggggggtgctg gaggctgctg gggtgaggta ctggctggag    3180
gggggcagcc tgctgggggc tgccaggcac ggggacatta tcccctggga ctatgatgtg    3240
gacctgggca tctacctgga ggatgtgggc aactgtgagc agctgagggg ggctgaggct    3300
ggctctgtgg tggatgagag gggctttgtg tgggagaagg ctgtggaggg ggactttttc    3360
agggtgcagt actctgagag caaccacctg cacgtggacc tgtggcccct ctaccccagg    3420
aatggggtga tgaccaagga cacctggctg gaccacaggc aggatgtgga gttccctgag    3480
cacttcctgc agcccctggt gcccctgccc tttgctggct ttgtggccca ggcccccaac    3540
aactacagga ggtcctgga gctgaagttt ggccctgggg tgattgagaa cccccagtac     3600
cccaacccctg ccctgctgag cctgacaggc tctggctgaa ttcaccccac cagtgcaggc    3660
tgcctatcag aaagtggtgg ctggtgtggc taatgccctg gcccacaagt atcactaagc    3720
tcgctttctt gctgtccaat ttctattaaa ggttcctttg ttccctaagt ccaactacta    3780
aactgggggga tattatgaag ggccttgagc atctggattc tgcctaataa aaaacattta    3840
ttttcattgc aatgatgtat ttaaattatt tctgaatatt ttactaaaaa gggaatgtgg    3900
gaggtcagtg catttaaaac ataaagaaat gaagagctag ttcaaacctt gggaaaatac    3960
actatatctt aaactccatg aaagaaggtg aggctgcaaa cagctaatgc acattggcaa    4020
cagccctgat gcctatgcct tattcatccc tcagaaaagg attcaagtag aggcttgatt    4080
tggaggttaa agttttgcta tgctgtattt tacattactt attgttttag ctgtcctcat    4140
gaatgtcttt tcactaccca tttgcttatc ctgcatctct cagccttgac tccactcagt    4200
tctcttgctt agagatacca cctttcccct gaagtgttcc tccatgtttt tacggcgaga    4260
tggtttctcc tcgcctggcc actcagcctt agttgtctct gttgtcttat agaggtctac    4320
ttgaagaagg aaaaacaggg ggcatggttt gactgtcctg tgagcccttc ttccctgcct    4380
cccccactca cagtgacccg gaatcaggaa ccccctagtga tggagttggc cactccctca    4440
ctgcgcgctc gctcgctcac tgaggccggg cgaccaaagg tcgcccgacg cccgggcttt    4500
gcccgggcgg cctcagtgag cgagcgagcg cgcagagagg gagtggccaa tttgagttct    4560
tctactcagg ttaaacttaa gcgcggccgc agtcctaggt tgcgcaatgg gcatgctaca    4620
gatcttccgc ggtgcagcaa gtcgactgca gaggcctgca tgcaagcttg gcgtaatcat    4680
ggtcatagct gtttcctgtg tgaaattgtt atccgctcac aattccacac aacatacgag    4740
ccggaagcat aaagtgtaaa gcctggggtg cctaatgagt gagctaactc acattaattg    4800
cgttgcgctc actgcccgct ttccagtcgg gaaacctgtc gtgccagctg cattaatgaa    4860
tcggccaacg cgcggggaga ggcggtttgc gtattgggcg ctcttccgct tcctcgctca    4920
ctgactcgct gcgctcggtc gttcggctgc ggcgagcggt atcagctcac tcaaaggcgg    4980
taatacggtt atccacagaa tcaggggata acgcaggaaa gaacatgtga gcaaaaggcc    5040
agcaaaaggc caggaaccgt aaaaaggccg cgttgctggc gtttttccat aggctccgcc    5100
cccctgacga gcatcacaaa aatcgacgct caagtcagag gtggcgaaac ccgacaggac    5160
tataaagata caggcgtttc ccccctggaa gctccctcgt gcgctctcct gttccgaccc    5220
tgccgcttac cggatacctg tccgcctttc tcccttcggg aagcgtggcg ctttctcata    5280
gctcacgctg taggtatctc agttcggtgt aggtcgttcg ctccaagctg ggctgtgtgc    5340
acgaaccccc cgttcagccc gaccgctgcg ccttatccgg taactatcgt cttgagtcca    5400
acccggtaag acacgactta tcgccactgg cagcagccac tggtaacagg attagcagag    5460
cgaggtatgt aggcggtgct acagagttct tgaagtggtg gcctaactac ggctacacta    5520
gaagaacagt atttggtatc tgcgctctgc tgaagccagt taccttcgga aaaagagttg    5580
gtagctcttg atccggcaaa caaaccaccg ctggtagcgg tggtttttt gtttgcaagc      5640
agcagattac gcgcagaaaa aaaggatctc aagaagatcc tttgatcttt tctacggggt     5700
ctgacgctca gtggaacgaa aactcacgtt aagggatttt ggtcatgaga ttatcaaaaa    5760
ggatcttcac ctagatcctt ttaaattaaa aatgaagttt taaatcaatc taaagtatat    5820
atgagtaaac ttggtctgac agttaccaat gcttaatcag tgaggcacct atctcagcga    5880
tctgtctatt tcgttcatcc atagttgcct gactccccgt cgtgtagata actacgatac    5940
gggagggctt accatctggc cccagtgctg caatgatacc gcgagaccca cgctcaccgg    6000
ctccagattt atcagcaata aaccagccag ccggaagggc cgagcgcaga agtggtcctg    6060
caactttatc cgcctccatc cagtctatta attgttgccg ggaagctaga gtaagtagtt    6120
cgccagttaa tagtttgcgc aacgttgttg ccattgctac aggcatcgtg gtgtcacgct    6180
cgtcgtttgg tatggcttca ttcagctccg gttcccaacg atcaaggcga gttacatgat    6240
cccccatgtt gtgcaaaaaa gcggttagct ccttcggtcc tccgatcgtt gtcagaagta    6300
agttggccgc agtgttatca ctcatggtta tggcagcact gcataattct cttactgtca    6360
tgccatccgt aagatgcttt tctgtgactg gtgagtactc aaccaagtca ttctgagaat    6420
agtgtatgcg gcgaccgagt tgctcttgcc cggcgtcaat acgggataat accgcgccac    6480
atagcagaac tttaaaagtg ctcatcattg gaaaacgttc ttcggggcga aaactctcaa    6540
ggatcttacc gctgttgaga tccagttcga tgtaacccac tcgtgcaccc aactgatctt    6600
cagcatcttt tactttcacc agcgtttctg ggtgagcaaa aacaggaagg caaaatgccg    6660
caaaaaaggg aataagggcg acacggaaat gttgaatact catactcttc ctttttcaat    6720
attattgaag catttatcag ggttattgtc tcatgagcgg atacatattt gaatgtattt    6780
agaaaaataa acaaataggg gttccgcgca catttccccg aaaagtgcca cctgacgtct    6840
aagaaaccat tattatcatg acattaacct ataaaaatag gcgtatcacg aggccctttc    6900
```

-continued

```
gtc                                                                    6903

SEQ ID NO: 12              moltype = DNA   length = 145
FEATURE                    Location/Qualifiers
misc_feature               1..145
                           note = Synthetic Polynucleotide
misc_feature               1..145
                           note = "ITR 5'"
source                     1..145
                           mol_type = other DNA
                           organism = synthetic construct
SEQUENCE: 12
ttggccactc cctctctgcg cgctcgctcg ctcactgagg ccgggcgacc aaaggtcgcc   60
cgacgcccgg gctttgcccg ggcggcctca gtgagcgagc gagcgcgcag agagggagtg  120
gccaactcca tcactagggg ttcct                                        145

SEQ ID NO: 13              moltype = DNA   length = 1061
FEATURE                    Location/Qualifiers
misc_feature               1..1061
                           note = Synthetic Polynucleotide
misc_feature               1..1061
                           note = "human desmin promoter"
source                     1..1061
                           mol_type = other DNA
                           organism = synthetic construct
SEQUENCE: 13
taccccctgc cccccacagc tcctctcctg tgccttgttt cccagccatg cgttctcctc   60
tataaatacc cgctctggta tttggggttg gcagctgttg ctgccaggga gatggttggg  120
ttgacatgcg gctcctgaca aaacacaaac ccctggtgtg tgtgggcgtg ggtggtgtga  180
gtaggggat gaatcaggga gggggcgggg gacccagggg gcaggagcca cacaaagtct   240
gtgcggggt gggagcgcac atagcaattg gaaactgaaa gcttatcaga ccctttctgg   300
aaatcagccc actgtttata aacttgaggc cccaccctcg acagtaccgg ggaggaagag   360
ggcctgcact agtccagagg gaaactgagg ctcagggcta gctcgcccat agacatacat  420
ggcaggcagg ctttggccag gatccctccg cctgccaggc gtctccctgc cctccttcc  480
tgcctagaga cccccaccct caagcctggc tggtctttgc ctgagaccca aacctcttcg  540
acttcaagag aatatttagg aacaaggtgg tttagggcct ttcctgggaa caggccttga   600
cccttaaga aatgacccaa agtctctcct tgaccaaaaa ggggaccctc aaactaaagg   660
gaagcctctc ttctgctgtc tcccctgacc ccactccccc ccaccccagg acgaggagat   720
aaccagggct gaaagaggcc cgcctggggg ctgcagacat gcttgctgcc tgccctggcg   780
aaggattggc aggcttgccc gtcacaggac ccccgctggc tgactcaggg gcgcaggcct   840
cttgcggggg agctggcctc cccgcccca cggccacggg ccgcccttc ctggcaggac    900
agcgggatct tgcagctgtc aggggagggg aggcggggc tgatgtcagg agggatacaa   960
atagtgccga cggctggggg ccctgtctcc cctcgccgca tccactctcc ggccggccgc  1020
ctgcccgccg cctcctccgt gcgcccgcca gcctcgcccg c                     1061

SEQ ID NO: 14              moltype = DNA   length = 452
FEATURE                    Location/Qualifiers
misc_feature               1..452
                           note = Synthetic Polynucleotide
misc_feature               1..452
                           note = "HBB2 intron followed by Kozak sequence"
source                     1..452
                           mol_type = other DNA
                           organism = synthetic construct
SEQUENCE: 14
gtacacatat tgaccaaatc agggtaattt tgcatttgta attttaaaaa atgctttctt   60
cttttaatat acttttttgt ttatcttatt tctaatactt tccctaatct ctttcttca   120
gggcaataat gatacaatgt atcatgcctc tttgcaccat tctaaagaat aacagtgata  180
atttctgggt taaggcaata gcaatatttc tgcatataaa tatttctgca tataaattgt  240
aactgatgta agaggtttca tattgctaat agcagctaca atccagctac cattctgctt   300
ttattttttg gttgggataa ggctggatta ttctgagtcc aagctaggcc cttttgctaa   360
tcttgttcat acctcttatc ttcctcccac agctcctggg caacgtgctg gtctctgtgc   420
tggcccatca ctttggcaaa gaattcgcca cc                                 452

SEQ ID NO: 15              moltype = DNA   length = 766
FEATURE                    Location/Qualifiers
misc_feature               1..766
                           note = Synthetic Polynucleotide
misc_feature               1..766
                           note = "HBB2 polyA"
source                     1..766
                           mol_type = other DNA
                           organism = synthetic construct
SEQUENCE: 15
attcacccca ccagtgcagg ctgcctatca gaaagtggtg ctggtgtgg ctaatgccct    60
ggcccacaag tatcactaag ctcgctttct tgctgtccaa tttctattaa aggttccttt  120
gttccctaag tccaactact aaactggggg atattatgaa gggccttgag catctggatt  180
ctgcctaata aaaaacattt attttcattg caatgatgta tttaaattat ttctgaatat  240
tttactaaaa agggaatgtg ggaggtcagt gcatttaaaa cataaagaaa tgaagagcta  300
```

-continued

```
gttcaaacct tgggaaaata cactatatct taaactccat gaaagaaggt gaggctgcaa   360
acagctaatg cacattggca acagccctga tgcctatgcc ttattcatcc ctcagaaaag   420
gattcaagta gaggcttgat ttggaggtta aagttttgct atgctgtatt ttacattact   480
tattgtttta gctgtcctca tgaatgtctt ttcactaccc atttgcttat cctgcatctc   540
tcagccttga ctccactcag ttctcttgct tagagatacc acctttcccc tgaagtgttc   600
cttccatgtt ttacggcgag atggtttctc ctcgcctggc cactcagcct tagttgtctc   660
tgttgtctta tagaggtcta cttgaagaag gaaaaacagg gggcatggtt tgactgtcct   720
gtgagccctt cttccctgcc tcccccactc acagtgaccc ggaatc                  766

SEQ ID NO: 16              moltype = DNA   length = 145
FEATURE                    Location/Qualifiers
misc_feature              1..145
                          note = Synthetic Polynucleotide
misc_feature              1..145
                          note = "ITR 3'"
source                    1..145
                          mol_type = other DNA
                          organism = synthetic construct
SEQUENCE: 16
aggaacccct agtgatggag ttggccactc cctctctgcg cgctcgctcg ctcactgagg   60
ccgggcgacc aaaggtcgcc cgacgcccgg gctttgcccg ggcggcctca gtgagcgagc   120
gagcgcgcag agagggagtg gccaa                                          145

SEQ ID NO: 17              moltype = DNA   length = 18
FEATURE                    Location/Qualifiers
misc_feature              1..18
                          note = Synthetic Polynucleotide
misc_feature              1..18
                          note = "Forward HBB2 polyA "
source                    1..18
                          mol_type = other DNA
                          organism = synthetic construct
SEQUENCE: 17
ccaggcgagg agaaacca                                                  18

SEQ ID NO: 18              moltype = DNA   length = 25
FEATURE                    Location/Qualifiers
misc_feature              1..25
                          note = Synthetic Polynucleotide
misc_feature              1..25
                          note = "Reverse HBB2 polyA "
source                    1..25
                          mol_type = other DNA
                          organism = synthetic construct
SEQUENCE: 18
cttgactcca ctcagttctc ttgct                                          25

SEQ ID NO: 19              moltype = DNA   length = 29
FEATURE                    Location/Qualifiers
misc_feature              1..29
                          note = Synthetic Polynucleotide
misc_feature              1..29
                          note = "Probe HBB2 polyA "
source                    1..29
                          mol_type = other DNA
                          organism = synthetic construct
SEQUENCE: 19
ctcgccgtaa aacatggaag gaacacttc                                      29

SEQ ID NO: 20              moltype = DNA   length = 1488
FEATURE                    Location/Qualifiers
misc_feature              1..1488
                          note = Synthetic Polynucleotide
misc_feature              1..1488
                          note = "WO2016/138387 (FKRP-06)"
source                    1..1488
                          mol_type = other DNA
                          organism = synthetic construct
SEQUENCE: 20
atgagactga caagatgcca ggccgccctg gccgctgcca tcacactgaa tctgctggtg   60
ctgttctatg tgtcctggct gcagcaccag ccccggaact ctagagccag aggccccaaga  120
agggcctctg ccgccggacc tagagtgaca gtgctcgtgc gcgagttcga ggccttcgac   180
aatgccgtgc ccgagctggt ggacagcttc ctgcagcaag accctgctca gcctgtggtg   240
gtggcgccga atacactgcc ttatcctcca ctggccctgc ccagaatccc caatgtgcag   300
ctggctctgc tgcagcccgc cctggataga cctgccgccg ctagcagacc tgagacatac   360
gtggccaccg agttcgtggc cctggtgcct gatggcgcca gagctgaagc tcccggcctg   420
ctggaaagaa tggtggaagc cctgagagcc ggcagcgcca gactggtggc tgctcctgtg   480
gctaccgcca accctgccag atgtctggcc ctgaatgtgt ccctgagaga gtggaccgcc   540
agatacggcg ctgcccctgc cgctcctaga tgtgatgctc tggatggcga cgccgtggtg   600
```

-continued

```
ctgctgagag ccagggacct gttcaacctg agcgcccctc tggccagacc tgtgggcaca    660
agcctgtttc tgcagacagc cctgaggggc tgggccgtgc agctgctgga tctgacattt    720
gccgctgcca gacagcctcc tctggccaca gcccatgcca gatggaaggc cgagagagag    780
ggcagagcca gaagggctgc tctgctgagg gccctgggca tcagactggt gtcttgggaa    840
ggcggcagac tcgagtggtt cggctgcaac aaagaaacca cccggtgctt cggcaccgtc    900
gtgggcgata caccagccta cctgtacag gaaagatgga cccccccttg ctgcctgcgg    960
gccctgagag aaacagccag atatgtcgtg ggcgtgctgg aagccgctgg cgtgcgatat   1020
tggctggaag gcggatctct gctgggagcc gccaggcacg cgacatcat cccttgggac   1080
tacgacgtgg acctgggcat ctacctggaa gatgtgggca actgcgagca gctgagaggc   1140
gccgaagccg gctctgtggt ggatgagagg ggcttcgtgt gggagaaggc cgtggaaggc   1200
gacttcttcc gggtgcagta cagcgagagc aaccatctgc atgtggacct gtggcccttc   1260
tacccccgga acgacgtgat gaccaaggac acctggctgg accaccggca ggacgtggaa   1320
ttccccgagc actttctgca gcccctggtg ccactgcctt tcgccggatt tgtggcccag   1380
gcccccaaca actaccggcg gttcctggaa ctgaagttcg gccctggcgt gatcgagaac   1440
ccccagtacc ctaaccctgc cctgctgagc ctgaccggca gcggctaa              1488

SEQ ID NO: 21            moltype = DNA   length = 6903
FEATURE                 Location/Qualifiers
misc_feature            1..6903
                        note = Synthetic Polynucleotide
misc_feature            1..6903
                        note = "pAAV-hDesmin-hFKRP-OPT08"
source                  1..6903
                        mol_type = other DNA
                        organism = synthetic construct
SEQUENCE: 21
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt accttaaacc    420
ggttcctaca tatgggttgc gcaatgcggc cgcagtactg cagaaatagg ccgaaatcgg    480
caaaatccct ttattggcca ctccctctct gcgcgctcgc tcgctcactg aggccggcg    540
accaaaggtc gcccgacgcc cgggctttgc ccgggcggcc tcagtgagcg agcgagcgcg    600
cagagaggga gtgggccaact ccatcactag gggttcctta ccccctgccc cccacagctc    660
ctctcctgtg ccttgtttcc cagccatgcg ttctcctcta taaataccCg ctctggtatt    720
tggggttggc agctgttgct gccagggaga tggttgggt gacatgcggc tcctgacaaa    780
acacaaaccc ctggtgtgtg tgggcgtggg tggtgtgagt aggggggatga atcagggagg    840
gggcggggga cccagggggc aggagccaca caaagtctgt gcgggggtgg gagcgcacat    900
agcaattgga aactgaaagc ttatcagacc ctttctggaa atcagcccac tgtttataaa    960
cttgaggccc caccctcgac agtaccgggg aggaagaggc cctgcactag tccagaggga   1020
aactgaggct cagggctagc tcgcccatag acatacatgg caggcaggct ttggccagga   1080
tccctccgcc tgccaggcgt ctccctgccc tccttcctg cctagagacc cccaccctca   1140
agcctggctg gtctttgcct gagacccaaa cctcttcgac ttcaagagaa tatttaggaa   1200
caaggtggtt taggggcttt cctgggaaca ggccttgacc ctttaagaaa tgacccaaag   1260
tctctccttg accaaaaagg ggaccctcaa actaaaggga agcctctctt ctgctgtctc   1320
ccctgacccc actccccccc accccaggac gaggagataa ccaggggctga aagaggcccg   1380
cctgggggct gcagacatgc ttgctgcctg ccctggcgaa ggattggcag gcttgcccgt   1440
cacaggaccc ccgctggctg actcagggggc gcaggcctct tgccgggggag ctggcctccc   1500
cgccccacg gccacgggcc gcccttcct ggcaggacag cgggatcttg cagctgtcag   1560
gggaggggag gcggggctg atgtcaggag ggatacaaat agtgccgacg gctggggcc   1620
ctgtctcccc tcgccgcatc cactctccgg ccggccgcct gccgccgcc tcctccgtgc   1680
gcccgccagc ctcgcccgcg tacacatatt gaccaaatca gggtaatttt gcatttgtaa   1740
ttttaaaaaa tgctttcttc ttttaatata cttttttgtt tatcttattt ctaatacttt   1800
ccctaatctc tttctttcag ggcaataatg atacaatgta tcatgcctct ttgcaccatt   1860
ctaaagaata acagtgataa tttctgggtt aaggcaatag caatatttct gcatataaat   1920
atttctgcat ataaattgta actgatgtaa gaggtttcat attgctaata gcagctacaa   1980
tccagctacc attctgcttt tattttttgg ttgggataag gctggattat tctgagtcca   2040
agctaggccc ttttgctaat cttgttcata cctcttatct tcctcccaca gctcctgggc   2100
aacgtgctgg tctctgtgct ggcccatcac tttggcaaag aattcgccac catgcggctc   2160
acccgctgcc aggctgccct ggctgctgcc atcaccctca accttctggt cctcttctat   2220
gtcagctggc tgcagcacca gcctaggaat tcccgggccc gagggcccct gagggcccc   2280
gctgctggcc ccaggggcac cgtcctggtg cgggagttcg aggcatttga caacgctgtg   2340
cccgagctgg tagactcctt cctgcagcaa gacccagccc agcccgtggt ggtggcagct   2400
gacaccctcc cctacccccc cctggccctg ccccgcatcc ccaacgtgag gctggccctg   2460
ctccagcccg ccctggaccg gccagctgca gccagccgcc ctgagaccta cgtggccacc   2520
gagtttgtgg ccctggtacc tgatgggggcc cgggctgagg cacctggcct ggtggagcgg   2580
atggtggagg ccctcagggc aggaagcgca aggctggtgg ctgccctgt tgccacagcc   2640
aaccctgcca ggtgcctggc cctgaacgtc agcctgcgag agtggaccgc ccgctacggg   2700
gcagcccccg ctgccccccg ctgcgacgcc ctggacggag atgctgtggt gctcctgagg   2760
gccagggacc tcttcaacct ctctgccccc ctggccggc ctgtgggcac cagcctcttt   2820
ctgcaacccg ccttagggg ctgggctgta cagctgctag acttgacctt cgctgctgcc   2880
cgccagcccc ccctggccac agcccacgcc cgctggaagg ctgagaggga gggaagggct   2940
cggcgggctg ccctgctcag ggccctggga atccgcctgg tgagctggga aggggggcgg   3000
ctggagtggt tcggctgcaa caaggagacc accgctgct tcggaaccgt ggtggggggac   3060
acccccgcct acctctacga ggagcgctgg acccccccct gctgcctgag ggccctgagg   3120
gagaccgccc gctatgtggt gggggtgctg gaggctgctg gggtgcgcta ctggctcgag   3180
```

-continued

```
ggggggctcac tgctgggggc tgcccgccac ggggacatca tcccatggga ctacgacgtg   3240
gacctgggca tctacttgga ggacgtgggc aactgcgagc agctgcgggg ggcagaggct   3300
ggctctgtgg tggatgagag gggcttcgta tgggagaagg ctgtggaggg ggactttttc   3360
agggtgcagt acagcgaaag caaccacttg cacgtggacc tgtggccctt ctaccccgc    3420
aatggggtca tgaccaagga cacctggctg gaccaccggc aggatgtgga gtttcccgag   3480
cacttcctgc agcccctggt gcccctgccc tttgctggct tcgtggccca ggcccctaac   3540
aactaccgcc gcttcctgga gctcaagttc gggcccgggg tgatcgagaa cccccagtac   3600
cccaaccctg cactgctgag tctgaccgga agcggctgaa ttcaccccac cagtgcaggc   3660
tgcctatcag aaagtggtgg ctggtgtggc taatgccctg gcccacaagt atcactaagc   3720
tcgctttctt gctgtccaat ttctattaaa ggttcctttg ttccctaagt ccaactacta   3780
aactgggggga tattatgaag ggccttgagc atctggattc tgcctaataa aaaacattta   3840
ttttcattgc aatgatgtat ttaaattatt tctgaatatt ttactaaaaa gggaatgtgg   3900
gaggtcagtg catttaaaac ataaagaaat gaagagctag ttcaaacctt gggaaaatac   3960
actatatctt aaactccatg aaagaaggtg aggctgcaaa cagctaatgc acattggcaa   4020
cagccctgat gcctatgcct tattcatccc tcagaaaagg attcaagtag aggcttgatt   4080
tggaggttaa agttttgcta tgctgtattt tacattactt attgtttag ctgtcctcat     4140
gaatgtcttt tcactaccca tttgcttatc ctgcatctct cagccttgac tccactcagt   4200
tctcttgctt agagatacca cctttcccct gaagtgttcc ttccatgttt tacggcgaga   4260
tggtttctcc tcgcctggcc actcagcctt agttgtctct gttgtcttat agaggtctac   4320
ttgaagaagg aaaaacaggg ggcatggttt gactgtcctg tgagcccttc ttccctgcct   4380
cccccactca cagtgacccg gaatcaggaa ccctagtga tggagttggc cactccctct   4440
ctgcgcgctc gctcgctcac tgaggccggg cgaccaaagg tcgcccgacg cccgggcttt   4500
gcccgggcgg cctcagtgag cgagcgagcg cgcagagagg gagtggccaa tttgagttct   4560
tctactcagg ttaaacttaa gcgcggccgc agtcctaggt tgcgcaatgg gcatgctaca   4620
gatcttccgc ggtgcagcaa gtcgactgca gaggcctgca tgcaagcttg gcgtaatcat   4680
ggtcatagct gtttcctgtg tgaaattgtt atccgctcac aattccacac aacatacgag   4740
ccggaagcat aaagtgtaaa gcctgggggtg cctaatgagt gagctaactc acattaattg   4800
cgttgcgctc actgcccgct ttccagtcgg gaaacctgtc gtgccagctg cattaatgaa   4860
tcggccaacg cgcggggaga ggcggtttgc gtattgggcg ctcttccgct tcctcgctca   4920
ctgactcgct gcgctcggtc gttcggctgc ggcgagcggt atcagctcac tcaaaggcgg   4980
taatacggtt atccacagaa tcaggggata acgcaggaaa gaacatgtga gcaaaaggcc   5040
agcaaaaggc caggaaccgt aaaaaggccg cgttgctggc gtttttccat aggctccgcc   5100
cccctgacga gcatcacaaa aatcgacgct caagtcagag gtggcgaaac ccgacaggac   5160
tataaagata ccaggcgttt ccccctggaa gctccctcgt gcgctctcct gttccgaccc   5220
tgccgcttac cggatacctg tccgcctttc tcccttcggg aagcgtggcg ctttctcata   5280
gctcacgctg taggtatctc agttcggtgt aggtcgttcg ctccaagctg ggctgtgtgc   5340
acgaacccc cgttcagccc gaccgctgcg ccttatccgg taactatcgt cttgagtcca     5400
acccggtaag acacgactta tcgccactgg cagcagccac tggtaacagg attagcagag   5460
cgaggtatgt aggcggtgct acagagttct tgaagtggtg gcctaactac ggctacacta   5520
gaagaacagt atttggtatc tgcgctctgc tgaagccagt taccttcgga aaaagagttg   5580
gtagctcttg atccggcaaa caaaccaccg ctggtagcgg tggtttttttt gtttgcaagc   5640
agcagattac gcgcagaaaa aaaggatctc aagaagatcc tttgatcttt tctacggggt   5700
ctgacgctca gtggaacgaa aactcacgtt aagggatttt ggtcatgaga ttatcaaaaa   5760
ggatcttcac ctagatcctt ttaaattaaa aatgaagttt taaatcaatc taaagtatat   5820
atgagtaaac ttggtctgac agttaccaat gcttaatcag tgaggcacct atctcagcga   5880
tctgtctatt tcgttcatcc atagttgcct gactccccgt cgtgtagata actacgatac   5940
gggagggctt accatctggc cccagtgctg caatgatacc gcgagaccca cgctcaccgg   6000
ctccagattt atcagcaata aaccagccag ccggaagggc cgagcgcaga gtggtcctg     6060
caactttatc cgcctccatc cagtctatta attgttgccg ggaagctaga gtaagtagtt   6120
cgccagttaa tagtttgcgc aacgttgttg ccattgctac aggcatcgtg gtgtcacgct   6180
cgtcgtttgg tatggcttca ttcagctccg gttcccaacg atcaaggcga gttacatgat   6240
ccccccatgtt gtgcaaaaaa gcggttagct ccttcggtcc tccgatcgtt gtcagaagta   6300
agttggccgc agtgttatca ctcatggtta tggcagcact gcataattct cttactgtca   6360
tgccatccgt aagatgcttt tctgtgactg gtgagtactc aaccaagtca ttctgagaat   6420
agtgtatgcg gcgaccgagt tgctcttgcc cggcgtcaat acgggataat accgcgccac   6480
atagcagaac tttaaaagtg ctcatcattg gaaaacgttc ttcggggcga aaactctcaa   6540
ggatcttacc gctgttgaga tccagttcga tgtaacccac tcgtgcaccc aactgatctt   6600
cagcatcttt tactttcacc agcgtttctg ggtgagcaaa aacaggaagg caaaatgccg   6660
caaaaaaggg aataaggggcg acacgaaaat gttgaatact cactcttc cttttttcaat    6720
attattgaag catttatcag ggttattgtc tcatgagcgg atacatattt gaatgtattt   6780
agaaaaataa acaaataggg gttccgcgca catttccccg aaaagtgcca cctgacgtct   6840
aagaaaccat tattatcatg acattaacct ataaaaatag gcgtatcacg aggcccttttc   6900
gtc                                                                 6903
```

POLYNUCLEOTIDES ENCODING A HUMAN FKRP PROTEIN

CROSS-REFERENCE TO RELATED APPLICATIONS

The present application is a continuation application of U.S. patent application Ser. No. 16/628,650, filed on Jan. 3, 2020, which is a U.S. National Phase under 35 U.S.C. § 371 of International Application PCT/EP2018/0068420, filed on Jul. 6, 2018, which claims the benefit of European Application No. 17305894.2, filed on Jul. 7, 2017, each of which is herein incorporated by reference in its entity.

REFERENCE TO SEQUENCE LISTING

A sequence listing submitted via ESF-Web is hereby incorporated by reference in accordance with 35 U S C. § 1.52(e). The name of the tile for the sequence listing is LAUR006.003C1, the date of creating of the file is Mar. 2, 2023, and the size of the file is 75.4 KB.

FIELD

The present invention provides an efficient gene therapy product for treating pathologies induced by a defect in α-dystroglycan (α-DG) glycosylation. It relates to poly-nucleotides encoding a human fukutin-related protein (FKRP) and containing mutation(s) avoiding supplementary transcript(s) generated from frameshift start codon(s). A higher level of expression of FKRP is observed with said polynucleotides, offering a valuable therapeutic tool for the treatment of various diseases linked to FKRP deficiencies, such as Limb-Girdle Muscular Dystrophy type 2I (LGMD2I).

BACKGROUND

The "Dystroglycanopathies" regroup different genetic pathologies leading to secondary aberrant glycosylation of α-dystroglycan (αDG). This protein, mostly present in skel-etal muscle, heart, eye and brain tissues, is a hyper-glyco-sylated membrane protein, the glycosylation process raising its weight from 70 to 156 kDa in muscle. It is part of the dystrophin-glycoprotein complex which connects the cyto-skeleton to the extracellular matrix (ECM). Its high glyco-sylation level enables αDG direct binding to the laminin globular domains of some ECM proteins, such as laminin in the cardiac and skeletal muscles, agrin and perlecan at the neuromuscular junction, neurexin in brain and pikachurin in the retina. Glycosylation of αDG is a complex process that is not yet fully understood. Indeed, a number of genes have been identified as being involved in αDG glycosylation. These discoveries have been accelerating recently thanks to the use of high throughput sequencing methods for mutation detection in patients showing αDG glycosylation defects. One of these proteins is the Fukutin-Related Protein (FKRP). It was originally classified as a putative αDG glycosyltransferase on account of the presence in its sequence of a DxD motif, which is common to many glycosyltransferases, and evidence of αDG hypoglycosy-lation in patients mutated in the FKRP gene (Breton et al., 1999; Brockington et al., 2001). Recently, FKRP and its homolog fukutin were identified as ribitol-5-phosphate (Rbo5P) transferases, forming a di-Rbo5P linker necessary for addition of the ligand binding moiety (Kanagawa et al., 2016).

Mutations in the FKRP gene can generate the entire range of pathologies induced by a defect in αDG glycosylation, from Limb-Girdle Muscular Dystrophy type 2I (LGMD2I; Muller et al., 2005); Congenital Muscular Dystrophy type 1C (MDC1C; Brockington et al., 2001) to Walker-Warburg Syndrome (WWS) and Muscle-Eye-Brain disease (MEB; Beltran-Valero de Bernabe et al., 2004). There is an inverse correlation between the severity of the disease and the number of patients, the more severe, the rarer the patients (prevalence indicated in www.orphanet.fr: WWS (all genes): 1-9/1,000,000 and LGMD2I: 1-9/100,000). The type of pathology seems, at least partially, correlated to the nature of the FKRP mutation. In particular, the homozygous L276I mutation, replacing a to leucine by an isoleucine in position 276 of the protein, is always associated with LGMD2I (Mercuri et al., 2003). LGMD2I is a recessive autosomal muscular dystrophy, affecting preferentially, albeit hetero-geneously, the muscles of the shoulder and pelvic girdles. It is one of the most frequent LGMD2 in Europe, notably due to high prevalence of the L276I mutation in Northern Europe (Sveen et al., 2006). The severity of the pathology is very heterogeneous. The muscular symptoms can appear between the first to third decades, and vary from Duchenne-like disease to relatively benign courses. The heart can also be affected with consequences such as severe heart failure and death (Muller et al., 2005). Investigations using cardiac magnetic resonance imaging suggest that a very high pro-portion of LGMD2I patients (60-80%) can present myocar-dial dysfunction such as reduced ejection fraction (Wahbi et al., 2008). Interestingly, the severity of the cardiac abnor-malities is not correlated to the skeletal muscle involvement.

Gicquel et al. (Hum Mol Genet, 2017 Mar. 3. doi: 10.1093/hmg/ddx066) reported the generation of a FKRP$^{L276I}$ mouse model in which the recombinant adeno-associated virus (rAAV2/9) transfer of the murine Fkrp gene, placed under the control of the desmin promoter and of the polyadenylation (polyA) signal of beta-hemoglobin (HBB2) gene, was evaluated. After intramuscular or intravenous delivery, improvement of the muscle pathology was observed. They obtained strong expression of FKRP, at mRNA as well as protein levels, and showed the rescue of αDG proper glycosylation and increase in laminin binding, that led to histological and functional rescue of the dystro-phy.

WO2016/138387 proposed to reduce the GC content of the wild-type nucleotide sequence encoding FKRP by about 5% to about 10% to increase expression of FKRP. It pro-vides a synthetic polynucleotide named SEQ ID NO: 1 having a GC content reduced by 9.99% in comparison to the wild-type sequence.

Therefore, gene replacement therapy based on FKRP appears as a promising treatment of pathologies resulting from a FKRP deficiency. However, there is still a need of improved treatments.

BRIEF SUMMARY

The present invention aims at alleviating or curing the devastating pathologies linked to a fukutin-related protein (FKRP) deficiency such as Limb-Girdle Muscular Dystro-phy type 2I (LGMD2I), by providing a native human FKRP protein encoded by a modified transgene which allows higher expression level of FKRP The present invention offers a promising gene therapy product based on a FKRP optimized sequence. The present application reports a higher level of FKRP in comparison with that obtained with the native coding sequence, when the claimed polynucleotides encapsidated in an AAV9 vector are intramuscularly injected in mice.

Definitions

Unless otherwise defined, all technical and scientific terms used therein have the same meaning as commonly understood by one of ordinary skill in the art. The terminology used in the description is for the purpose of describing particular embodiments only and is not intended to be limiting.

The articles "a" and "an" are used herein to refer to one or to more than one (i.e., to at least one) of the grammatical object of the article. By way of example, "an element" means one element or more than one element.

"About" or "approximately" as used herein when referring to a measurable value such as an amount, a temporal duration, and the like, is meant to encompass variations of 20% or 10%, more preferably 5%, even more preferably 1%, and still more preferably +0.1% from the specified value, as such variations are appropriate to perform the disclosed methods.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

A "nucleotide sequence encoding an amino acid sequence" includes all nucleotide sequences that are degenerate versions of each other and that encode the same amino acid sequence. The phrase nucleotide sequence that encodes a protein or a RNA or a cDNA may also include introns to the extent that the nucleotide sequence encoding the protein may in some version contain an intron(s).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the noncoding strand, used as the template for transcription of a gene or cDNA, can be referred to as encoding the protein or other product of that gene or cDNA.

The term "start codon» designates the first codon of a messenger RNA (mRNA) transcript translated by a ribosome. The start codon always codes for methionine in eukaryotes. The most common start codon is AUG. As a consequence, on the coding strand (or sense strand or non-template strand) of DNA, the sequence of the start codon is ATG. The corresponding anticodon on the noncoding strand (or antisense strand or anticoding strand or template strand or transcribed strain) is CAT. In the rest of the description, the term "start codon" is also used in relation to DNA.

The term "polynucleotide" as used herein is defined as a chain of nucleotides which can be single-stranded (ss) or double-stranded (ds). Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A protein may be "altered" and contain deletions, insertions, or substitutions of amino acid residues which produce a silent change and result in a functionally equivalent. Deliberate amino acid substitutions may be made on the basis of similarity in polarity, charge, solubility, hydrophobicity, hydrophilicity, and/or the amphipathic nature of the residues as long as the biological activity is retained. For example, negatively charged amino acids may include aspartic acid and glutamic acid, positively amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

A "variant", as used herein, refers to an amino acid sequence that is altered by one or more amino acids. The variant may have "conservative" changes, wherein a substituted amino acid has similar structural or chemical properties, e.g. replacement of leucine with isoleucine. A variant may also have "non-conservative" changes, e.g. replacement of a. glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art.

"Identical" or "homologous" refers to the sequence identity or sequence similarity between two polypeptides or between two nucleic acid molecules. When a position in both of the two compared sequences is occupied by the same base or amino acid monomer subunit, e.g., if a position in each of two DNA molecules is occupied by adenine, then the molecules are homologous or identical at that position. The percent of homology/identity between two sequences is a function of the number of matching positions shared by the two sequences divided by the number of positions compared×100. For example, if 6 of 10 of the positions in two sequences are matched then the two sequences are 60% identical. Generally, a comparison is made when two sequences are aligned to give maximum homology/identity.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence, which is required for expression of a gene product operably linked to the promoter/regulatory sequence. In some instances, this sequence may be the core promoter sequence and in other instances, this sequence may also include an enhancer sequence and other regulatory elements, which are required for expression of the gene product. The promoter/regulatory sequence may, for example, be one, which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell preferentially if the cell is a cell of the tissue type corresponding to the promoter.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics, which are normal or expected for one cell or tissue type, might be abnormal for a different cell or tissue type.

The terms "patient," "subject," "individual," and the like are used interchangeably herein, and refer to any animal, or cells thereof whether in vitro or in situ, amenable to the methods described herein. A subject can be a mammal, e.g. a human, a dog, but also a mouse, a rat or a nonhuman primate. In certain non-limiting embodiments, the patient, subject or individual is a human.

A "disease" or a "pathology" is a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

A disease or disorder is "alleviated" or "ameliorated" if the severity of a symptom of the disease or disorder, the frequency with which such a symptom is experienced by a patient, or both, is reduced. This also includes halting progression of the disease or disorder. A disease or disorder is "cured" if the severity of a symptom of the disease or disorder, the frequency with which such a symptom is experienced by a patient, or both, is eliminated.

A "therapeutic" treatment is a treatment administered to a subject who exhibits signs of pathology, for the purpose of diminishing or eliminating those signs. A "prophylactic" treatment is a treatment administered to a subject who does not exhibit signs of pathology or has not be diagnosed for the pathology yet, for the purpose of preventing or postponing the occurrence of those signs.

As used herein, "treating a disease or disorder" means reducing the frequency or severity of at least one sign or symptom of a disease or disorder experienced by a subject. Disease and disorder are used interchangeably herein in the context of treatment.

An "effective amount" of a compound is that amount of compound which is sufficient to provide a beneficial effect to the subject to which the compound is administered. The phrase "therapeutically effective amount", as used herein, refers to an amount that is sufficient or effective to prevent or treat (delay or prevent the onset of, prevent the progression of, inhibit, decrease or reverse) a disease or condition, including alleviating symptoms of such diseases. An "effective amount" of a delivery vehicle is that amount sufficient to effectively bind or deliver a compound.

BRIEF DESCRIPTION OF THE DRAWINGS

FIG. 2A shows evaluation of the FKRP expression by western-blotting. FIG. 2B shows quantification of the FKRP protein after normalization with GADPH. FIG. 2C shows quantification of the FKRP protein after normalization with GADPH: administration of FKRP wt (SEQ ID NO: 2), FKRP-OPTcomp (SEQ ID NO: 4), FKRP-06 (SEQ ID NO: 20), FKRP-OPT-07 (SEQ ID NO: 5), FKRP-OPT-08 (SEQ ID NO: 6), FKRP-OPT-10 (SEQ ID NO: 7), and FKRP-OPT-11 (SEQ ID NO: 8), at the dose of 3E9 vg/TA.

FIG. 3A shows centronucleation index in the TA muscle. FIG. 3B shows force of TA in situ. FIG. 3C shows results of an Escape Test.

DETAILED DESCRIPTION

Figure 1:
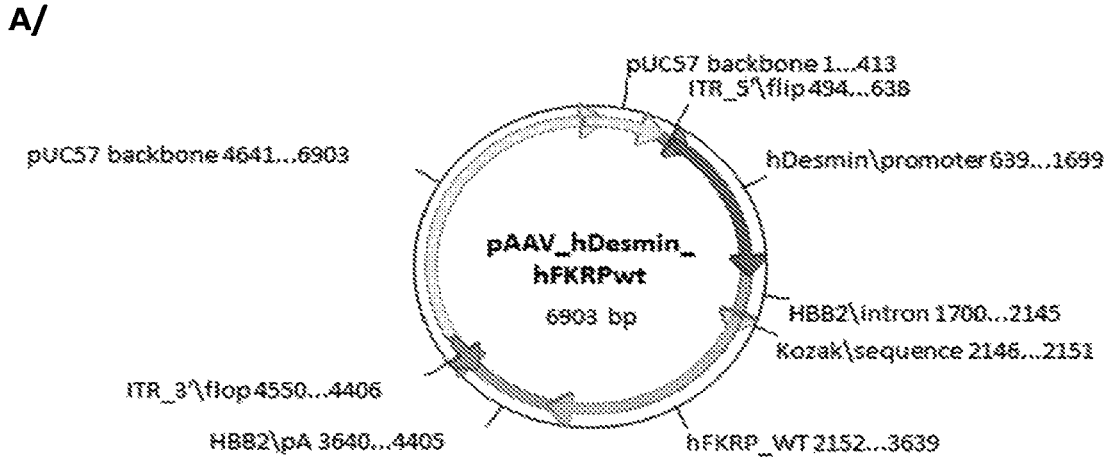
FIG. 1: Scheme of the plasmids used in this study: Panel A/pAAV-hDesmin-hFKRPwt; Panel B/pAAV-hDesmin-hFKRP-OPTmin; Panel C/pAAV-hDesmin-hFKRP-OPT-comp.
Figure 1:
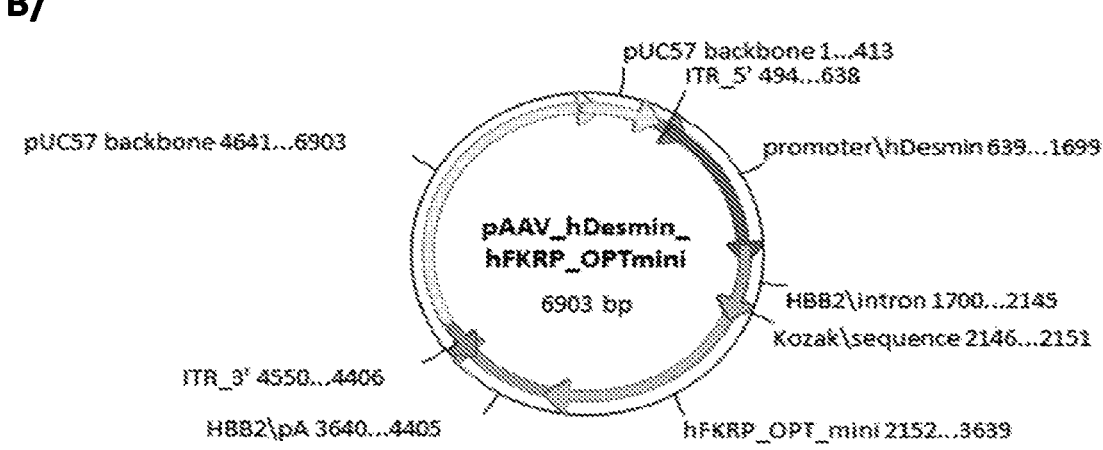
Figure 1:
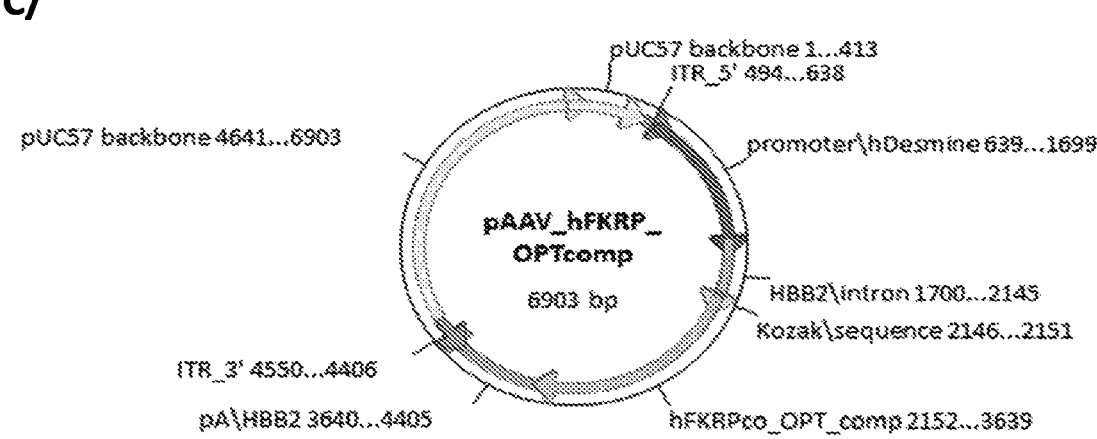

The present invention is based on the finding that the suppression of supplementary frameshift start codon(s) contained in the coding region of the Fukutin-related protein (FKRP) increases FKRP expression.

Accordingly, in one aspect, the invention provides a synthetic polynucleotide encoding a human FKRP, wherein said polynucleotide contains at least a mutation avoiding supplementary transcript(s) generated from frameshift start codon(s).

According to the invention, the synthetic polynucleotide comprises or consists of a nucleic acid sequence encoding a functional human FKRP.

In one embodiment, the polynucleotide encoding the human FKRP, also named ORF for "open reading frame", is a cDNA. However, e.g. single- or double-stranded DNA or RNA can be used.

In the frame of the invention, a human FKRP protein is a protein consisting of or comprising the sequence shown in SEQ ID NO: 1 (corresponding to a protein of 495 aa).

According to specific embodiments, a functional human FKRP is a protein having the same functions as the native human FKRP encoded by SEQ ID NO: 1, especially the ability to glycosylate α-dystroglycan (αDG) and/or to alleviate, at least partially, one or more of the symptoms associated with a defect in FKRP, especially the LGMD2I phenotype as disclosed above. It can be a fragment and/or a derivative thereof. According to one embodiment, said FKRP sequence has identity greater than or equal to 60%, 70%, 80%, 90%, 95% or even 99% with sequence SEQ ID NO: 1.

As known in the art, the native human sequence encoding the human FKRP protein of sequence SEQ ID NO: 1 has the sequence SEQ ID NO: 2.

The present invention excludes the native sequence SEQ ID NO: 2 and is focused on sequences encoding SEQ ID NO: 1 but different from SEQ ID NO: 2. More precisely, the native polynucleotide (SEQ ID NO: 2) has been modified or optimized: Based on the degeneracy of the genetic code, one or more base(s) of the native sequence (SEQ ID NO: 2) have been substituted by other bases(s) while not changing the resulting amino acid sequence (SEQ ID NO: 1). In other words, the present invention provides a synthetic polynucleotide, i.e. a polynucleotide which is not naturally occurring, advantageously optimized.

According to another specific embodiment, a synthetic polynucleotide according to the invention does not consist of or comprise the sequence SEQ ID NO: 20, or any sequence having at least 90% identity thereto.

Preferably, the synthetic polynucleotide encoding a human FKRP is about 60% homologous/identical, more preferably about 65%, 70%, 75%, 80%, 81%, 82%, 83%, 84%, 85%, 86%, 87%, 88%, 88%, 89% or about 90%, 91%, 92%, 93%, 94% homologous/identical, even more preferably, about 95% homologous/identical, and even more preferably about 96%, 97%, 98% or even 99% homologous/identical to a nucleotide sequence of an isolated nucleic acid encoding a functional human FKRP (preferably of sequence SEQ ID NO: 1), especially of sequence SEQ ID NO: 2. As previously mentioned, said polynucleotide does not comprise or does not consist of the sequence SEQ ID NO: 2.

As known in the art, a coding sequence can contain frameshift start codon(s) in a sense or antisense direction, which can generate alternative or supplementary transcription products. As an example, the coding sequence may contain further ATG in case of sense start codons, or CAT in case of an antisense start codon. According to a specific embodiment, these start codons are frameshift, i.e. they generate alternative Open Reading Frames (ORF) which are not in phase/frame with the coding sequence of the human FKRP, but shifted by one nucleotide ("phase/frame+1") or 2 nucleotides ("phase/frame+2"). In other words, the so-called "frameshift" start codon(s) are in one of the alternative frames of the FKRP coding sequence.

In the specific case of SEQ ID NO: 2: The main ORF starts at position 1 with a ATG (nucleotides 1 to 3 of SEQ ID NO: 2) encoding a Methionine (M or Met); the corresponding ORF is composed of 1488 bases or nucleotides, encodes a 495 aa protein and ends by a stop codon TGA. Further ORFs in phase, i.e. in frame, start at positions 430 (nucleotides 430 to 432 of SEQ ID NO: 2) and 1279 (nucleotides 1279 to 1281 of SEQ ID NO: 2) with a ATG encoding a Methionine (M or Met). It is however not possible to change them since no other codon than ATG codes for a Methionine classically.

In phase+1, there are 4 start codons able to generate supplementary transcripts:

CAT at position 429 (nucleotides 429 to 431 of SEQ ID NO: 2), 819 (nucleotides 819 to 821 of SEQ ID NO: 2) and 1431 (nucleotides 1431 to 1433 of SEQ ID NO: 2) corresponding to ATG in the antisense direction;

ATG at position 545 (nucleotides 545 to 547 of SEQ ID NO: 2), in the sense direction.

There is no potential start codon (sense or antisense) in phase/frame+2.

According to the invention, at least one base change is introduced in order to mutate the start codon but without changing the encoded amino acids.

According to an embodiment, the polynucleotide has one start codon mutated, said start codon being located at position 429 ("429-431"), or 545 ("545-547"), or 819 ("819-821"), or 1431 ("1431-1433") of sequence SEQ ID NO: 2.

In a preferred embodiment, the polynucleotide has at least one start codon mutated, said start codon being located at position 819 ("819-821") of sequence SEQ ID NO: 2.

According to another embodiment, the polynucleotide has at least two (2) start codons mutated, said start codons being located at position 429 and 545, or 429 and 819, or 429 and 1431, or 545 and 819 or 545 and 1431, or 819 and 1431 of sequence SEQ ID NO: 2. Advantageously, the mutated start codons is located at positions 429 and 819, 545 and 819, or 819 and 1431 of sequence SEQ ID NO: 2.

According to still another embodiment, the polynucleotide has at least three (3) start codons mutated, said start codons being located at position 429 and 545 and 819, or 429 and 545 and 1431, or 429 and 819 and 1431, or 545 and 819 and 1431 of sequence SEQ ID NO: 2, advantageously at position 429, 819 and 1431 of sequence SEQ ID NO: 2.

More advantageously, the polynucleotide consists of or comprises the sequence SEQ ID NO: 4, or SEQ ID NO: 7, or SEQ ID NO: 8.

According to still another embodiment, the polynucleotide has at least four (4) start codons mutated, said start codons being located at position 429 and 545 and 819 and 1431 of sequence SEQ ID NO: 2. Advantageously, the polynucleotide consists of or comprises the sequence SEQ ID NO: 3, or SEQ ID NO: 5, or SEQ ID NO: 6.

The modification of the start codon can result from 1, 2 or 3 mutations in said codon. As already mentioned, said mutations should not change the encoded sequence.

The suppression of the antisense start codon located at position 429 ("429-431") can e.g. result from the change of the C base located at position 429 into G or A. As a consequence, the "CAT" (ATG in the antisense direction) is converted into "GAT" (ATC in the antisense direction) or "AAT" (ATT in the antisense direction), which does not correspond to a start codon in the antisense direction anymore but does not change the corresponding amino acid sequence.

The suppression of the sense start codon located at position 545 ("545-547") can e.g. result from the change of the T base located at position 546 into C. As a consequence, the "ATG" is converted into "ACG", which does not correspond to a start codon in the sense direction anymore but does not change the corresponding amino acid sequence.

The suppression of the antisense start codon located at position 819 ("819-821") can e.g. result from the change of the C base located at position 819 into G or A. As a consequence, the "CAT" (ATG in the antisense direction) is converted into "GAT" (ATC in the antisense direction) or "AAT" (ATT in the antisense direction), which does not correspond to a start codon in the antisense direction anymore but does not change the corresponding amino acid sequence.

The suppression of the antisense start codon located at position 1431 ("1431-1433") can e.g. result from the change of the C base located at position 1431 into G. As a consequence, the "CAT" (ATG in the antisense direction) is converted into "GAT" (ATC in the antisense direction), which does not correspond to a start codon in the antisense direction anymore but does not change the corresponding amino acid sequence.

The polynucleotide of the invention can be further optimized as follows:

According to one embodiment, the GC content is modified, advantageously decreased. Preferably the GC content of the polynucleotide of the invention is reduced by less than 5% relative to the GC content of SEQ ID NO: 2 or by more than 10% relative to the GC content of SEQ ID NO: 2. While replacing the G and C bases by A or T, the amino acid sequence should be conserved and preferably no additional start codon is introduced.

According to another embodiment, the CG motifs are replaced to avoid CpG islets formation preferably with the same precautions as disclosed above (the amino acid sequence is conserved and no additional start codon is introduced).

According to another embodiment, the sequence is optimized based on transfer RNA frequencies in human, e.g. following the codon frequency table disclosed in Sharp et al. (1988), preferably with the same precautions as disclosed above.

According to another embodiment, the polynucleotide of the invention may further have at least a mutation in the region 553-559 of SEQ ID NO: 2 (GCCCCCG), which corresponds to a stem-loop. Advantageously, the stem-loop structure is modified or even destroyed because of the mutation(s). As an example, the nucleotide C at position 558 of SEQ ID NO: 2 is converted into T.

According to a specific embodiment, the polynucleotide of the invention consists of or comprises a sequence selected among SEQ ID NO: 3, SEQ ID NO: 4, SEQ ID NO: 5, SEQ ID NO: 6, SEQ ID NO: 7 and SEQ ID NO: 8, or a sequence being about 60% homologous/identical, more preferably about 65%, 70%, 75%, 80%, 81%, 82%, 83%, 84%, 85%, 86%, 87%, 88%, 88%, 89% or about 90%, 91%, 92%, 93%, 94% homologous/identical, even more preferably, about 95% homologous/identical, and even more preferably about 96%, 97%, 98% or even 99% homologous/identical thereto.

According to a preferred embodiment, said homologous sequence has the same start codons mutated.

Accordingly and as an example, the present invention also relates to a sequence having 60% identity, more preferably about 65%, 70%, 75%, 80%, 81%, 82%, 83%, 84%, 85%, 86%, 87%, 88%, 88%, 89% or about 90%, 91%, 92%, 93%, 94% identity, even more preferably, about 95% identity, and even more preferably about 96%, 97%, 98% or even 99% identity to SEQ ID NO: 4 and having 3 start codons mutated at position 429, 819 and 1431 of sequence SEQ ID NO: 2. According to a specific embodiment, said sequence is SEQ ID NO: 7 or SEQ ID NO: 8.

According to another example, the present invention also relates to a sequence having 60% identity, more preferably about 65%, 70%, 75%, 80%, 81%, 82%, 83%, 84%, 85%, 86%, 87%, 88%, 88%, 89% or about 90%, 91%, 92%, 93%, 94% identity, even more preferably, about 95% identity, and even more preferably about 96%, 97%, 98% or even 99% identity to SEQ ID NO: 6 and having 4 start codons mutated at position 429, 545, 819 and 1431 of sequence SEQ ID NO: 2. According to a specific embodiment, said sequence is SEQ ID NO: 5 or SEQ ID NO: 3.

According to a specific embodiment, the isolated polynucleotide is inserted into a vector. In brief summary, the expression of natural or synthetic nucleic acids is typically achieved by operably linking a nucleic acid or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

In one embodiment, the vector is an expression vector, advantageously a viral vector.

In one embodiment, the viral vector is selected from the group consisting of a baculoviral vector, herpes viral vector, lentiviral vector, retroviral vector, adenoviral vector, and adeno-associated viral (AAV) vector.

According to a specific embodiment of the invention, the viral vector containing the polynucleotide is an adeno-associated viral (AAV) vector.

Adeno-associated viral (AAV) vectors have become powerful gene delivery tools for the treatment of various disorders. AAV vectors possess a number of features that render them ideally suited for gene therapy, including a lack of pathogenicity, moderate immunogenicity, and the ability to transduce post-mitotic cells and tissues in a stable and efficient manner. Expression of a particular gene contained within an AAV vector can be specifically targeted to one or more types of cells by choosing the appropriate combination of AAV serotype, promoter, and delivery method.

In one embodiment, the encoding sequence is contained within an AAV vector. More than 100 naturally occurring serotypes of AAV are known. Many natural variants in the AAV capsid exist, allowing identification and use of an AAV with properties specifically suited for dystrophic pathologies. AAV viruses may be engineered using conventional molecular biology techniques, making it possible to optimize these particles for cell specific delivery of nucleic acid sequences, for minimizing immunogenicity, for tuning stability and particle lifetime, for efficient degradation, for accurate delivery to the nucleus.

As mentioned above, the use of AAV vectors is a common mode of exogenous delivery of DNA as it is relatively non-toxic, provides efficient gene transfer, and can be easily optimized for specific purposes. Among the serotypes of AAVs isolated from human or non-human primates (NHP) and well characterized, human serotype 2 is the first AAV that was developed as a gene transfer vector. Other currently used AAV serotypes include AAV1, AAV3, AAV4, AAV5, AAV6, AAV7, AAV8, AAV9, AAVrh10, AAV11 and AAV12. In addition, non-natural engineered variants and chimeric AAV can also be useful.

Desirable AAV fragments for assembly into vectors include the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells.

Such fragments may be used alone, in combination with other AAV serotype sequences or fragments, or in combination with elements from other AAV or non-AAV viral sequences. As used herein, artificial AAV serotypes include, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid. Thus exemplary AAVs, or artificial AAVs, include AAV2/8 (U.S. Pat. No. 7,282,199), AAV2/5 (available from the National Institutes of Health), AAV2/9 (WO2005/033321), AAV2/6 (U.S. Pat. No. 6,156,303), and AAVrh10 (WO2003/042397), among others. In one embodiment, the vectors useful in the compositions and methods described herein contain, at a minimum, sequences encoding a selected AAV serotype capsid, e.g., an AAV8 capsid, or a fragment thereof. In another embodiment, useful vectors contain, at a minimum, sequences encoding a selected AAV serotype rep protein, e.g., AAV8 rep protein, or a fragment thereof. Optionally, such vectors may contain both AAV cap and rep proteins. In vectors in which both AAV rep and cap are provided, the AAV rep and AAV cap sequences can both be of one serotype origin, e.g., all AAV8 origin. Alternatively, vectors may be used in which the rep sequences are from an AAV serotype, which differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector, such as AAV2/8 (U.S. Pat. No. 7,282,199).

According to one embodiment, the composition comprises an AAV of serotype 2, 5, 8 or 9. Advantageously, the claimed vector is an AAV8 or AAV9 vector, especially an AAV2/8 or AAV2/9 vector. More advantageously, the claimed vector is an AAV9 vector or an AAV2/9 vector.

In the AAV vectors used in the present invention, the AAV genome may be either a single stranded (ss) nucleic acid or a double stranded (ds)/self complementary (sc) nucleic acid molecule.

Advantageously, the polynucleotide encoding the human FKRP is inserted between the ITR («Inverted Terminal Repeat») sequences of the AAV vector. Typical ITR sequences correspond to SEQ ID NO: 12 (5'ITR sequences) and SEQ ID NO: 16 (3'ITR sequences).

Recombinant viral particles can be obtained by any method known to the one skilled in the art, e.g. by co-transfection of 293 HEK cells, by the herpes simplex virus system and by the baculovirus system. The vector titers are usually expressed as viral genomes per mL (vg/mL).

In one embodiment, the vector comprises regulatory sequences, especially a promoter sequence. Such promoters can be natural or synthetic (artificial) promoters, inducible or constitutive.

In one embodiment, the promoter is a ubiquitous promoter or having a low tissue-specificity. As an example, the expression vector can harbor the phosphoglycerate kinase 1 (PGK), EF1, β-actin, CMV promoter.

In a preferred embodiment, the promoter sequence is chosen in order to adequately govern the expression of the nucleic acid sequence placed under its control, in terms of expression level, but also of tissue specificity. In one embodiment, the expression vector comprises a muscle specific promoter. Such a promoter allows a robust expression in the skeletal muscles, and possibly in the cardiac muscle (heart). Examples of suitable promoters known by the skilled person are e.g. the desmin promoter, the muscle creatine kinase (MCK) promoter, the CK6 promoter, the Syn promoter, the ACTA1 promoter or the synthetic promoter C5-12 (spC5-12). Of particular interest is the human desmin promoter as shown in sequence SEQ ID NO: 13.

The FKRP promoter can also be used.

A non-exhaustive list of other possible regulatory sequences is:

sequences for transcript stabilization, e.g. intron 1 of hemoglobin (HBB2). As shown in sequence SEQ ID NO: 14, said HBB2 intron is advantageously followed by consensus Kozak sequence included before AUG start codon within mRNA, to improve initiation of translation;

a polyadenylation signal, e.g. the polyA of the gene of interest, the polyA of SV40 or of beta hemoglobin (HBB2), advantageously in 3' of the sequence encoding the human FKRP. As a preferred example, the poly A of HBB2 is disclosed in sequence SEQ ID NO: 15; enhancer sequences;

miRNA target sequences, which can inhibit the expression of the sequence encoding the human FKRP in non target tissues, in which said expression is not desired, for example where it can be toxic. Preferably, the corresponding miRNA is not present in the skeletal muscles, and possibly not in the heart.

Typically, a vector according to the invention comprises:

5'ITR sequences (SEQ ID NO: 12) corresponding to nucleotides 494 to 638 of SEQ ID NO: 10 or 11; followed by the human desmin promoter (SEQ ID NO: 13) corresponding to nucleotides 639 to 1699 of SEQ ID NO: 10 or 11; followed by the HBB2 intron followed by consensus Kozak sequence (SEQ ID NO: 14) corresponding to nucleotides 1700 to 2151 of SEQ ID NO: 10 or 11; followed by the polynucleotide encoding the human FKRP, e.g. SEQ ID NO: 3 or 4 or 5 or 6 or 7 or 8, corresponding to nucleotides 2152 to 3639 of SEQ ID NO: 10 or 11 in case of SEQ ID NO: 3 and 4; followed by the HBB2 polyA sequence (SEQ ID NO: 15) corresponding to nucleotides 3640 to 4405 of SEQ ID NO: 10 or 11; followed by 3'ITR sequences (SEQ ID NO: 16) corresponding to nucleotides 4406 to 4550 of SEQ ID NO: 10 or 11.

In relation to a polynucleotide having the sequence SEQ ID NO: 3, SEQ ID NO: 4 and SEQ ID NO: 6, a vector of the invention comprises the sequences shown in SEQ ID NO: 10, SEQ ID NO: 11, and SEQ ID NO: 21 respectively.

According to one embodiment, the invention relates to a vector, advantageously an expression vector, more advantageously an AAV vector harboring the sequence SEQ ID NO: 10, SEQ ID NO: 11 or SEQ ID NO: 21. As mentioned above, the invention also encompasses homologous sequences, that is, displaying about 60% homology, more preferably about 70% homology, even more preferably about 80% homology, more preferably about 90% homology, even more preferably about 95% homology, and even more preferably about 97%, 98% or even 99% homology to the sequence SEQ ID NO: 10, SEQ ID NO: 11 or SEQ ID NO: 21.

Further aspects of the invention concern:

A cell comprising the polynucleotide of the invention or a vector comprising said polynucleotide, as disclosed above.

The cell can be any type of cells, i.e. prokaryotic or eukaryotic. The cell can be used for propagation of the vector or can be further introduced (e.g. grafted) in a host or a subject. The polynucleotide or vector can be introduced in the cell by any means known in the art, e.g. by transformation, electroporation or transfection. Vesicles derived from cells can also be used.

A transgenic animal, advantageously non-human, comprising the polynucleotide of the invention, a vector comprising said polynucleotide, or a cells comprising said polynucleotide or said vector, as disclosed above.

Another aspect of the invention relates to a composition comprising a polynucleotide, a vector or a cell, as disclosed above, for use as a medicament.

According to an embodiment, the composition comprises at least said gene therapy product (the polynucleotide, the vector or the cell), and possibly other active molecules (other gene therapy products, chemical molecules, peptides, proteins . . . dedicated to the treatment of the same disease or another disease.

The present invention then provides pharmaceutical compositions comprising a polynucleotide, a vector or a cell of the invention. Such compositions comprise a therapeutically effective amount of the therapeutic (the polynucleotide or vector or cell of the invention), and a pharmaceutically acceptable carrier. In a specific embodiment, the term "pharmaceutically acceptable" means approved by a regulatory agency of the Federal or a state government or listed in the U.S. or European Pharmacopeia or other generally recognized pharmacopeia for use in animals, and humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsions, sustained-release formulations and the like. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the subject.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to release pain at the site of the injection.

In one embodiment, the composition according to the invention is suitable for administration in humans. The composition is preferably in a liquid form, advantageously a saline composition, more advantageously a phosphate buffered saline (PBS) composition or a Ringer-Lactate solution.

The amount of the therapeutic (i.e. a nucleic acid or a vector or a cell) of the invention which will be effective in the treatment of the target diseases can be determined by standard clinical techniques. In addition, in vivo and/or in vitro assays may optionally be employed to help predict optimal dosage ranges. The precise dose to be employed in the formulation will also depend on the route of administration, the weight and the seriousness of the disease, and should be decided according to the judgment of the practitioner and each patient's circumstances.

Suitable administration should allow the delivery of a therapeutically effective amount of the gene therapy product to the target tissues, especially skeletal muscles and possibly heart. In the context of the invention, when the gene therapy product is a viral vector comprising a polynucleotide encoding a human FKRP, the therapeutic dose is defined as the quantity of viral particles (vg for viral genomes) containing the to FKRP sequence, administered per kilogram (kg) of the subject.

Available routes of administration are topical (local), enteral (system-wide effect, but delivered through the gastrointestinal (GI) tract), or parenteral (systemic action, but delivered by routes other than the GI tract). The preferred route of administration of the compositions disclosed herein is parenteral which includes intramuscular administration (i.e. into the muscle) and systemic administration (i.e. into the circulating system). In this context, the term "injection" (or "perfusion" or "infusion") encompasses intravascular, in particular intravenous (IV), intramuscular (IM), intraocular or intracerebral administration. Injections are usually performed using syringes or catheters.

In one embodiment, systemic delivery of the composition comprises administering the composition near a local treatment site, i.e. in a vein or artery nearby a weakened muscle. In certain embodiments, the invention comprises the local delivery of the composition, which produces systemic effects. This route of administration, usually called "regional (loco-regional) infusion", "administration by isolated limb perfusion" or "high-pressure transvenous limb perfusion" has been successfully used as a gene delivery method in muscular dystrophy (Fan et al., 2012).

According to one aspect, the composition is administered to an isolated limb (loco-regional) by infusion or perfusion. In other words, the invention comprises the regional delivery of the composition in a leg and/or arm by an intravascular route of administration, i.e. a vein (transveneous) or an artery, under pressure. This is usually achieved by using a tourniquet to temporarily arrest blood circulation while allowing a regional diffusion of the infused product, as e.g. disclosed by Toromanoff et al. (2008).

In one embodiment, the composition is injected in a limb of the subject. When the subject is a human, the limb can be the arm or the leg. According to one embodiment, the composition is administered in the lower part of the body of the subject, e.g. below the knee, or in the upper part of the body of the subject, e.g., below the elbow.

In one embodiment, the composition is administered to a peripheral vein, e.g. the cephalic vein. The volume of the composition to be infused can be in a range that varies between about 5 and 40% of the limb volume. The typical dose can vary between 5 and 30 ml/kg of body weight. In one embodiment, the pressure to be applied (tourniquet pressure or to maximum line pressure) is below 100 000 Pa, advantageously below 50 000 Pa. In a preferred embodiment, the pressure applied is around 300 torr (40 000 Pa).

In one embodiment, the blood circulation of the limb is stopped using a tourniquet that is tightened for several minutes to more than one hour, typically between about 1 and 80 minutes, for example about 30 minutes. In a preferred embodiment, the tourniquet was applied before, during and after the administration, for example about 10 minutes prior to, about 20 minutes during and about 15 min after the infusion. More generally, the pressure is applied for several minutes, typically between about 1 and 80 minutes, for example about 30 minutes. In a preferred embodiment, the pressure is applied before, during and after the administration, for example about 10 minutes prior to, about 20 minutes during and about 15 minutes after the infusion.

In one embodiment, the average flow rate is comprised between 5 and 150 ml/min, advantageously between 5 and 80 ml/min, for example 10 ml/min. Of course, the flow rate also determines the time period during which the blood circulation is stopped and the pressure applied.

In the context of a loco-regional administration, the dose injected may vary between $10^{12}$ and $10^{14}$ vg/kg of the patient body, preferably between $10^{12}$ and $10^{13}$ vg/kg.

A preferred method of administration according to the invention is systemic administration. Systemic injection opens the way to an injection of the whole body, in order to reach the entire muscles of the body of the subject including the heart and the diaphragm and then a real treatment of these systemic and still incurable diseases. In certain embodiments, systemic delivery comprises delivery of the composition to the subject such that composition is accessible throughout the body of the subject.

According to a preferred embodiment, systemic administration occurs via injection of the composition in a blood vessel, i.e. intravascular (intravenous or intra-arterial) administration. According to one embodiment, the composition is administered by intravenous injection, through a peripheral vein.

The systemic administration is typically performed in the following conditions:
a flow rate of between 1 to 10 mL/min, advantageously between 1 to 5 mL/min, e.g. 3 mL/min;
the total injected volume can vary between 1 and 20 mL, preferably 5 mL of vector preparation per kg of the subject. The injected volume should not represent more than 10% of total blood volume, preferably around 6%.

When systemically delivered, the composition is preferably administered with a dose less than or equal to $10^{15}$ vg/kg or even $10^{14}$ vg/kg, advantageously between $10^{12}$ vg/kg and $10^{14}$ vg/kg, more advantageously between $5 \cdot 10^{12}$ vg/kg and $10^{14}$ vg/kg, e.g. 1, 2, 3, 4, 5, 6, 7, 8 or $9 \cdot 10^{13}$ vg/kg. A lower dose of e.g. 1, 2, 3, 4, 5, 6, 7, 8 or $9 \cdot 10^{12}$ vg/kg can also be contemplated in order to avoid potential toxicity and/or immune reactions. As known by the skilled person, a dose as low as possible giving a satisfying result in term of efficiency is preferred.

In a specific embodiment, the treatment comprises a single administration of the composition.

"Dystroglycanopathy" means a disease or pathology linked to an aberrant glycosylation of α-dystroglycan (αDG). This defect can be due to a FKRP defect. According to a specific embodiment, the pathology is selected in the group consisting of: Limb-Girdle Muscular Dystrophy type 2I (LGMD2I), Congenital Muscular Dystrophy type 1C (MDC1C), Walker-Warburg Syndrome (WWS) and Muscle-Eye-Brain disease (MEB), advantageously LGMD2I.

Subjects that could benefit from the compositions of the invention include all patients diagnosed with such a disease or at risk of developing such a disease. A subject to be treated can then be selected based on the identification of mutations or deletions in the FKRP gene by any method known to the one skilled in the art, including for example sequencing of the FKRP gene, and/or through the evaluation of the FKRP level of expression or activity by any method known to the one skilled in the art. Therefore, said subjects include both subjects already exhibiting symptoms of such a disease and subjects at risk of developing said disease. In one embodiment, said subjects include subjects already exhibiting symptoms of such a disease. In another embodiment, said subjects are ambulatory patients and early non-ambulant patients.

Such compositions are notably intended for gene therapy, particularly for the treatment of Limb-Girdle Muscular Dystrophy type 2I (LGMD2I), Congenital Muscular Dystrophy type 1C (MDC1C), Walker-Warburg Syndrome (WWS) and Muscle-Eye-Brain disease (MEB), advantageously LGMD2I.

According to one embodiment, the present invention concerns a method of treatment of a dystroglycanopathy comprising administering to a subject the gene therapy product (polynucleotide, vector or cell), as disclosed above.

Advantageously, the dystroglycanopathy is a pathology linked to an aberrant glycosylation of α-dystroglycan (αDG) and/or a FKRP deficiency. More advantageously, the pathology is Limb-Girdle Muscular Dystrophy type 2I (LGMD2I), Congenital Muscular Dystrophy type 1C (MDCIC), Walker-Warburg Syndrome (WWS) or Muscle-Eye-Brain disease (MEB).

In an additional aspect, the invention provides a method of increasing glycosylation of α-dystroglycan (αDG) in a cell comprising delivering to said cell the polynucleotide or the vector of the invention, wherein the synthetic polynucleotide is expressed in said cell, thereby producing FKRP and increasing glycosylation of αDG.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002).

These techniques are applicable to the production of the polynucleotides and polypeptides of the invention, and, as such, may be considered in making and practicing the invention.

Particularly useful techniques for particular embodiments will be discussed in the sections that follow.

The disclosures of each and every patent, patent application, and publication cited herein are hereby incorporated herein by reference in their entirety.

Without further description, it is believed that one of ordinary skill in the art can, using the preceding description and the following illustrative examples, make and utilize the compounds of the present invention and practice the claimed methods.

Examples

The invention is further described in detail by reference to the following experimental examples and the attached figures. These examples are provided for purposes of illustration only, and are not intended to be limiting.

Materials and Methods

Design of the Novel Human FKRP Sequences:

The human FKRP coding sequence SEQ ID NO: 2 has been modified according to the following rules:

introduction of mutations suppressing the sense and antisense frameshift ATG present in the coding region, at positions 429 (antisense; phase+1), 546 (sense; phase+1), 819 (antisense; phase+1) and/or 1431 (antisense; phase+1);

possibly following the codon frequency table as e.g. disclosed in Sharp et al. (1988);

without generation of new Open-Reading-Frame (ORF);

possibly replacing CG motives to avoid CpG islets formation;

possibly decreasing GC %;

possibly modifying the stem-loop present at position 553-559 of SEQ ID NO: 2.

All the resulting designed sequences (SEQ ID NO: 3 to 8 shown in Table 1 below) encode a FKRP protein having sequence SEQ ID NO: 1, corresponding to the human native FKRP sequence.

Plasmids and AAV Vectors:

The coding sequence of the human Fkrp gene (SEQ ID NO: 2) was synthesized using classical gene synthesis service methodology, and inserted into a plasmid (pUC57) containing AAV2 ITRs, the human desmin promoter, the HBB2 intron followed by Kozak sequence, and the HBB2 polyA (Hemoglobin subunit 02 polyadenylation signal).

The resulting plasmid, shown in FIG. 1, panel A, is called pAAV-hDesmin-hFKRPwt. The sequence of the insert including the ITR sequences is shown in SEQ ID NO: 9.

Plasmids pAAV-hDesmin-hFKRP-OPTmin (FIG. 1, panel B) and pAAV-hDesmin-hFKRP-OPTcomp (FIG. 1, panel C), whose insert sequence is shown in SEQ ID NO: 10 and 11 respectively, have been obtained by replacing the coding sequence of the native human FKRP protein (SEQ ID NO: 2) by the modified sequences SEQ ID NO: 3 and 4, respectively. The other plasmids FKRP-06, FKRP-OPT-07, FKRP-OPT-08, FKRP-OPT-10 and FKRP-OPT-11 have been obtained in a similar way by replacing SEQ ID NO: 2 by sequence SEQ ID NO: 20, SEQ ID NO: 5, SEQ ID NO: 6, SEQ ID NO: 7 and SEQ ID NO: 8, respectively.

Adenovirus free rAAV2/9 viral preparations were generated by packaging AAV2-ITR recombinant genomes in AAV9 capsids, using a three plasmids transfection protocol as previously described (Bartoli et al., 2006). Briefly, HEK293 cells were cotransfected with pAAV-hDesmin-hFKRPwt (or pAAV-hDesmin-hFKRP-OPTmin or pAAV-hDesmin-hFKRP-OPTcomp), a RepCap plasmid (pAAV2.9, Dr J. Wilson, UPenn) and an adenoviral helper plasmid (pXX6; Apparailly et al., 2005) at a ratio of 1:1:2. Crude viral lysate was harvested at 60 hr post-transfection and lysed by freeze-and-thaw cycles. The viral lysate was purified through two rounds of CsCl ultracentrifugation followed by dialysis. Viral genomes were quantified by a TaqMan real-time PCR assay using primers and probes corresponding to the HBB2polyA of the AAV vector genome. The primer pairs and TaqMan probes used for amplification were:

```
                                    (SEQ ID NO: 17)
   Forward: CCAGGCGAGGAGAAACCA (SEQ ID NO: 18)
   Reverse: CTTGACTCCACTCAGTTCTCTTGCT;
   and (SEQ ID NO: 19)
   Probe: CTCGCCGTAAAACATGGAAGGAACACTTC.
```

Western-Blotting

Cell pellets and muscle tissues were mechanically homogenized in RIPA lysis buffer (Thermo Fisher Scientific, Waltham, MA, USA), complemented with Complete protease inhibitor cocktail EDTA-free (Roche, Bile, Switzerland). Nucleic acids contained in the samples were degradated by incubation 15 minutes at 37° C. with benzonase (Sigma, St. Louis, MO, USA).

Proteins were separated using precast polyacrylamide gel (4-15%, BioRad, Hercules, CA, USA) and then transferred to nitrocellulose membrane.

Rabbit polyclonal antibody against FKRP has been previously described (Gicquel et al., 2017). Nitrocellulose membranes were probed with antibodies against FKRP (1:100) and GAPDH (Santa Cruz Biotechnologies, Dallas, TX, USA, 1:200) for normalization, for 2 hours at room temperature.

Finally, membranes were incubated with IRDye® for detection by the Odyssey infrared-scanner (LI-COR Biosciences, Lincoln, NE, USA).

Animals and Injections

One month-old mice were used. All animals of this study were handled according to the European guidelines for the human care and use of experimental animals, and all procedures on animals were approved by Genopole's ethics committee.

For the evaluation of gene transfer efficiency, male C57B16 mice were injected intramuscularly into the TA (Tibialis Anterior) muscle with a volume of 25 µL, at two different doses: 3 E9 vg/TA and 1.5 E10 vg/TA. As a negative control, mice were injected with the buffer used for the AAV formulation, i.e. PBS. Mice were euthanized after 1 month and the injected muscles were dissected out and frozen in isopentane cooled in liquid nitrogen.

For in vivo functional tests, AAV9-FKRP containing FKRP-OPTcomp sequence (SEQ ID NO: 4) was administrated by intravenous injection to HSA-FKRPdel mice, a FKRP-deficient mouse model, at 2 doses: 2.5 E12 vg/kg and 1 E13 vg/kg. After 3 months, the animals were submitted to different functional tests.

In Vivo Evaluation

Escape Test:

The global strength of mice is evaluated by the escape test (Carlson and Makiejus, 1990). Briefly, mice are placed on a platform facing the entrance of a 30 cm-long tube. A cuff wrapped around the tail is connected to a fixed force transducer and the mice are induced to escape within the tube in the direction opposite from the force transducer by a gentle pinching of the tail. A short peak of force is induced by this flight forward and the average of the five highest force peaks normalized by body weight are analyzed. Material used:

Force transducer ADInstrument MLT1030 serial 810.

Software ADinstrument Labchart7.

Force of TA In Situ:

Skeletal muscle function is evaluated by the measure of muscle contraction in situ, as previously described (Vignaud et al., 2005). Animals are anesthetized by intra-peritoneal injection of Ketamine (100 mg/kg) and Xylazine (10 mg/kg) and supplemental doses are administered as required to maintain deep anaesthesia. The knee and foot are fixed with clamps and stainless steel pins. The TA muscle is exposed and the distal tendon is cut and attached to a force transducer (Aurora Scientific, Dublin, Ireland). The sciatic nerves are proximally crushed and distally stimulated by a bipolar silver electrode using supra-maximal square wave pulses of 0.1 ms duration. Absolute maximal forces are determined at optimal length (length at which maximal tetanic tension is observed). The specific maximal force is calculated by normalizing the total muscle force with the muscle mass. Material used:

Apparatus Aurora Scientific.

Sensor 305C 5N Cambridge Technology Model 6650 n° X11271243Y. Software ASI 610A Dynamic muscle Control.

Centronucleation Index:

Injected mice were sacrificed soon after the functional tests. Skeletal muscles were sampled and frozen in cooled isopentane. Transverse cryosections were stained with Hematoxylin-Phloxine-Saffron (HPS) and were used for centronucleated fibers numeration. The number of centronucleated fibers was reported to the slice area to obtain the centronucleation index.

Results:

I/Design of Novel Human FKRP Sequences:

In order to evaluate the impact of modifications in the FKRP coding sequence, a series of sequences encoding the human FKRP protein of sequence SEQ ID NO: 1, derived from the sequence SEQ ID NO: 2, have been designed and synthetized. The main features of said sequences are summarized in Table 1:

TABLE 1

| Characteristics of the modified sequences encoding the human FKRP protein | | | |
| --- | --- | --- | --- |
| Name | Sequence | Base at position | Stem-loop at position 553-559 |
| FKRP wt | SEQ ID NO: 2 | 429: C 546: T 819: C 1431: C | Preserved |
| FKRP-OPTmin | SEQ ID NO: 3 | 429: G 546: C 819: A 1431: G | Preserved |
| FKRP-OPTcomp | SEQ ID NO: 4 | 429: G 546: T 819: G 1431: G | Modified |
| FKRP-OPT-07 | SEQ ID NO: 5 | 429: G 546: C 819: A 1431: G | Preserved |
| FKRP-OPT-08 | SEQ ID NO: 6 | 429: G 546: C 819: A 1431: G | Preserved |
| FKRP-OPT-10 | SEQ ID NO: 7 | 429: G 546: T 819: G 1431: G | Modified |
| FKRP-OPT-11 | SEQ ID NO: 8 | 429: A 546: T 819: G 1431: G | Modified |
| FKRP-06 (WO2016/138387) | SEQ ID NO: 20 | 429: A 546: C 819: C 1431: G | Modified |

Figures 2A, 2B:
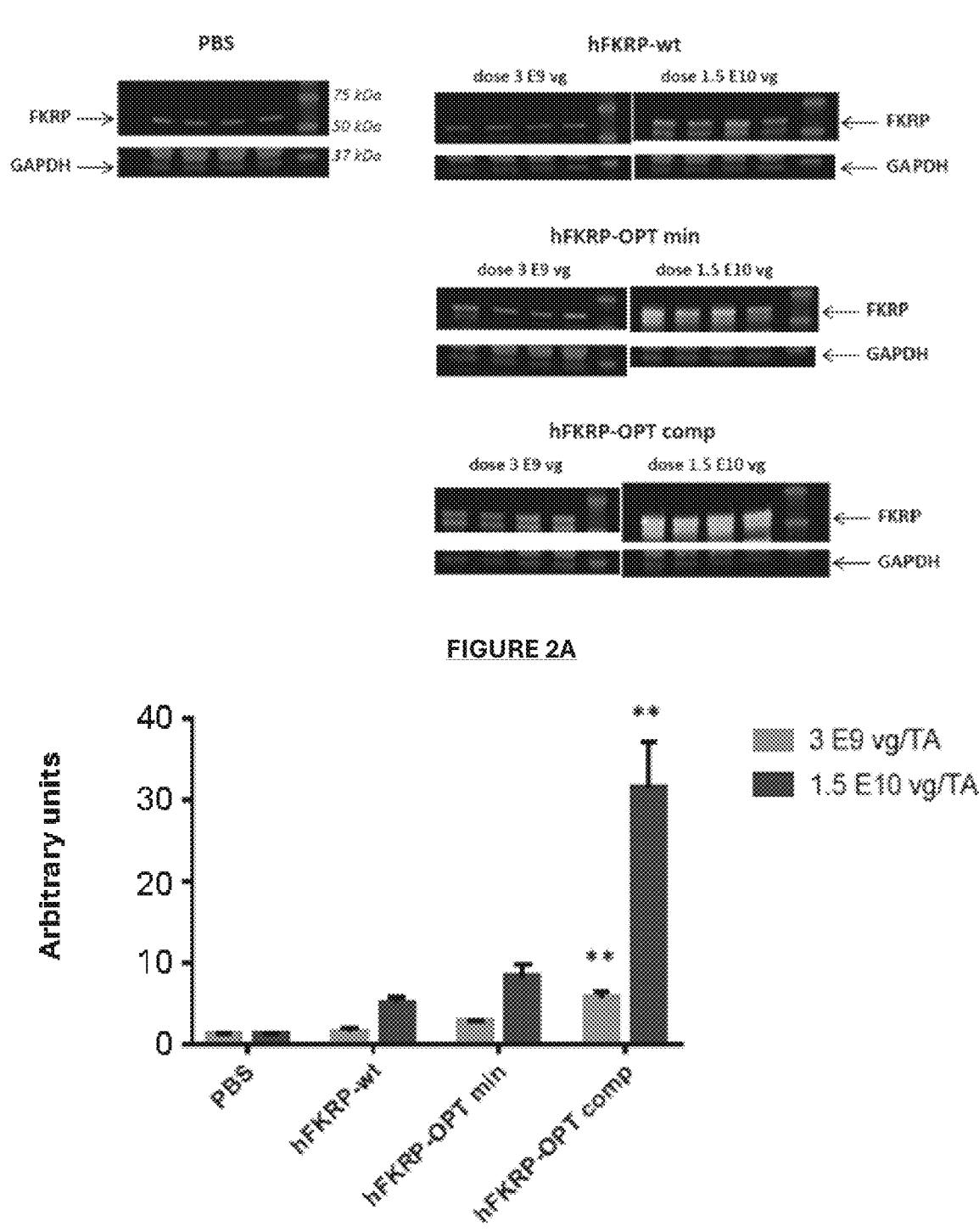
FIGS. 2A-2C: Injection of C57Bl6 mice without (PBS) or with AAV9 comprising different forms of the human FKRP (hFKRP) transgene: hFKRP-wt (coding sequence SEQ ID NO: 2), hFKRP-OPTmin (coding sequence SEQ ID NO: 3) and hFKRP-OPTcomp (coding sequence SEQ ID NO: 4) at 2 different doses (3E9 vg/TA and 1.5E10 vg/TA).

II/Evaluation of the Constructs In Vivo:

FIG. 2A shows the results obtained by western-blot on FKRP expression after gene transfer. The FKRP protein expressed from the different constructs (wt and optimized) has the expected size (58 kDa). Moreover, the modified FKRP transgenes allow a higher expression of the FKRP protein in comparison with the wild type sequence. The intensity of the obtained bands was quantified and normalized by the GAPDH normalizer. The quantification indicates a 5 fold increase for hFKRP-OPTcomp compared to FKRP wt (FIG. 2B).

Figure 2C:
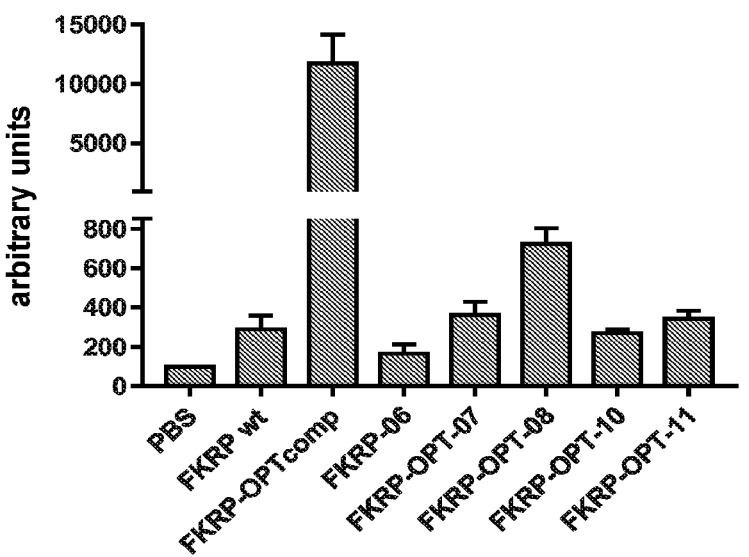

The same experiments were repeated with the different FKRP sequences shown in table 1, including the sequence disclosed in WO2016/138387 (SEQ ID NO: 1 in said document; SEQ ID NO: 20 in the present application). As illustrated in FIG. 2C, the sequence disclosed in WO2016/138387 (noted FKRP-06) does not allow reaching the level of transgene expression observed with the constructs according to the invention. Among the newly tested sequences, FKRP-08 is the best candidate but they generally lead to a level of transgene expression higher than the native sequence.

II/Functional Evaluation of the Constructs:

The best candidate, i.e. FKRP-OPTcomp (SEQ ID NO: 4), has been tested for its in vivo efficiency in a FKRP-deficient mouse model.

Figure 3A:
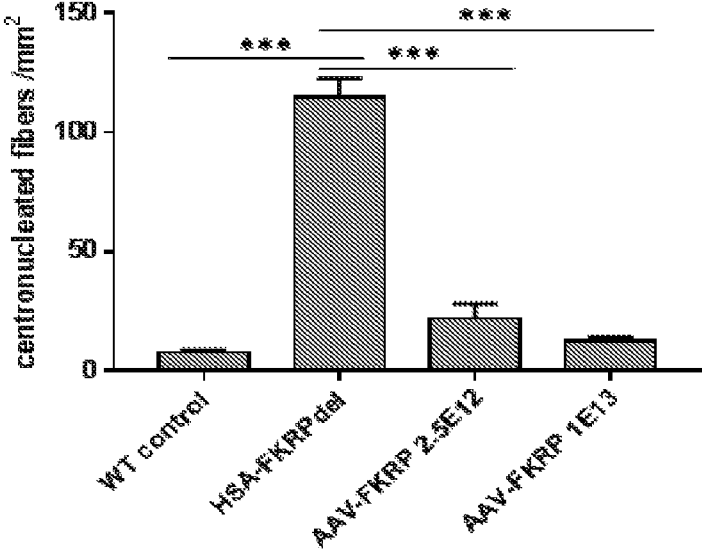
FIGS. 3A-3C: In vivo evaluation of FKRP-OPTcomp (SEQ ID NO: 4) after administration to HSA-FKRPdel mice (a FKRP-deficient mouse model) at 2 different doses (3E9 vg/TA and 1.5E10 vg/TA).
Figure 3B:
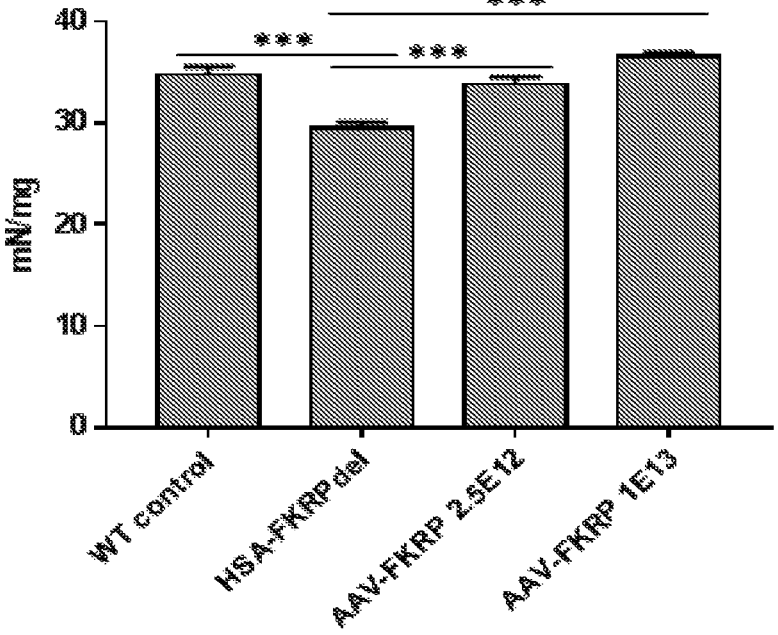
Figure 3C:
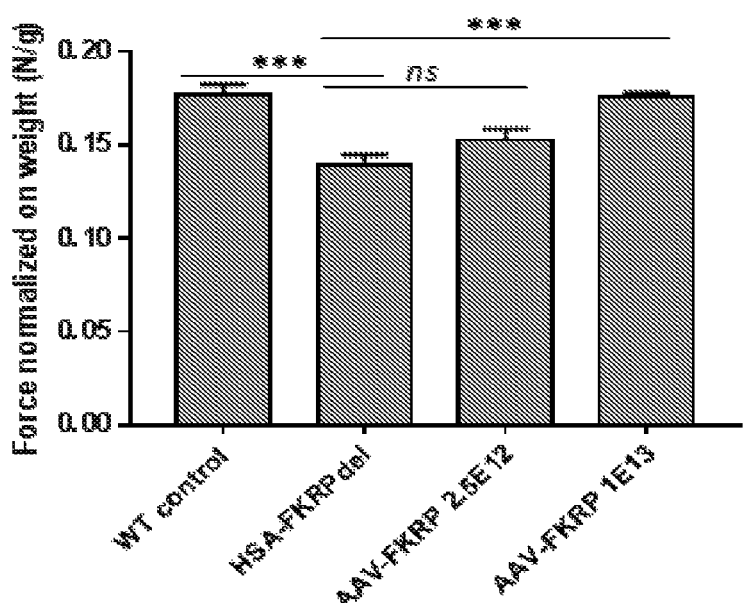

The data of FIG. 3A reveal a reduction of centronucleation in treated animals. Moreover, the in situ measurement of the force of the tibialis anterior (TA) muscle (FIG. 3B) and of the global strength evaluated by the escape test (FIG. 3C) reveal an improvement of the muscle function in treated animals.

CONCLUSIONS

C/Results of an Escape Test.

The present study shows that sequence optimization of the human FKRP transgene allows an improved level of FKRP expression after intramuscular injection of AAV vectors harboring said transgenes in mice. This increase is of therapeutic and clinical interest since it ameliorates the efficacy of the treatment and/or allows decreasing the injected doses of the therapeutic product.

REFERENCES

Apparailly, F., Khoury, M., Vervoordeldonk, M. J., Adriaansen, J., Gicquel, E., Perez, N., Riviere, C., Louis-Plence, P., Noel, D., Danos, O. et al. (2005) Adeno-associated virus pseudotype 5 vector improves gene transfer in arthritic joints. Hum. Gene Ther., 16, 426-434.

Bartoli, M., Poupiot, J., Goyenvalle, A., Perez, N., Garcia, L., Danos, O. and Richard, I. (2006) Noninvasive monitoring of therapeutic gene transfer in animal models of muscular dystrophies. Gene Ther., 13, 20-28.

Beedle, A. M., Turner, A. J., Saito, Y., Lueck, J. D., Foltz, S. J., Fortunato, M. J., Nienaber, P. M. and Campbell, K. P. (2012) Mouse fukutin deletion impairs dystroglycan processing and recapitulates muscular dystrophy. J. Clin. Invest., 122, 3330-3342.

Beltran-Valero de Bernabe, D., Voit, T., Longman, C., Steinbrecher, A., Straub, V., Yuva, Y., Herrmann, R., Sperner, J., Korenke, C., Diesen, C. et al. (2004) Mutations in the FKRP gene can cause muscle-eye-brain disease and Walker-Warburg syndrome. J. Med. Genet., 41, e61.

Breton, C. and Imberty, A. (1999) Structure/function studies of glycosyltransferases. Curr. Opin. Struct. Biol., 9, 563-571.

Brockington, M., Blake, D. J., Prandini, P., Brown, S. C., Torelli, S., Benson, M. A., Ponting, C. P., Estournet, B., Romero, N. B., Mercuri, E. et al. (2001) Mutations in the fukutin-related protein gene (FKRP) cause a form of congenital muscular dystrophy with secondary laminin alpha2 deficiency and abnormal glycosylation of alpha-dystroglycan. Am. J. Hum. Genet., 69, 1198-1209.

Gicquel et al. (2017) Hum Mol Genet, doi: 10.1093/hmg/ddx066.

Kanagawa, M., Kobayashi, K., Tajiri, M., Manya, H., Kuga, A., Yamaguchi, Y., Akasaka-Manya, K., Furukawa, J. I., Mizuno, M., Kawakami, H. et al. (2016) Identification of a Post-translational Modification with Ribitol-Phosphate and Its Defect in Muscular Dystrophy. Cell reports, in press.

Mercuri, E., Brockington, M., Straub, V., Quijano-Roy, S., Yuva, Y., Herrmann, R., Brown, S. C., Torelli, S., Dubowitz, V., Blake, D. J. et al. (2003) Phenotypic spectrum associated with mutations in the fukutin-related protein gene. Ann. Neurol., 53, 537-542.

Muller, T., Krasnianski, M., Witthaut, R., Deschauer, M. and Zierz, S. (2005) Dilated cardiomyopathy may be an early sign of the C826A Fukutin-related protein mutation. Neuromuscul. Disord., 15, 372-376.

Rohr, U. P., Wulf, M. A., Stahn, S., Steidl, U., Haas, R. and Kronenwett, R. (2002) Fast and reliable titration of recombinant adeno-associated virus type-2 using quantitative real-time PCR. J. Virol. Methods, 106, 81-88.

Sharp, P. M., Cowe E., Higgins D. G., Shields D. C, Wolfe K. H, Wright F (1988) Codon usage patterns in *Escherichia coli, Bacillus subtilis, Saccharomyces cerevisiae, Schizosaccharomyces pombe, Drosophila melanogaster* and *Homo sapiens*; a review of the considerable within-species diversity. Nucleic Acids Res., 16(17):8207-11.

Sveen, M. L., Schwartz, M. and Vissing, J. (2006) High prevalence and phenotype-genotype correlations of limb girdle muscular dystrophy type 2I in Denmark. Ann. Neurol., 59, 808-815.

Toromanoff et. al. (2008), Molecular Therapy 16(7):1291-99.

Wahbi, K., Meune, C., Hamouda el, H., Stojkovic, T., Laforet, P., Becane, H. M., Eymard, B. and Duboc, D. (2008) Cardiac assessment of limb-girdle muscular dystrophy 2I patients: an echography, Holter ECG and magnetic resonance imaging study. Neuromuscul. Disord., 18, 650-655.

Zheng Fan et al. (2012), Molecular Therapy 20(2), 456-461.

What is claimed is:

1. A synthetic polynucleotide encoding a human fukutin-related protein (FKRP) comprising an amino acid sequence as set forth in SEQ ID NO: 1, wherein:

the polynucleotide has at least three antisense start codons mutated, said antisense start codons being located at position 429, 819, and 1431 of sequence SEQ ID NO: 2; and the polynucleotide comprises a nucleic acid sequence as set forth in SEQ ID NO: 6.

2. A vector comprising the polynucleotide according to claim 1.

3. The vector according to claim 2, wherein the vector comprises a sequence as set forth in SEQ ID NO: 21, or a sequence having at least 90% identity thereto.

4. The vector according to claim 2, wherein the vector is an adeno-associated viral (AAV) vector.

5. The vector according to claim 4, wherein the AAV vector is of serotype 9.

6. The vector according to claim 4, wherein the AAV vector is serotype 2, 8, or 9.

7. The vector according to claim 4, wherein the AAV vector is serotype 2/9.

8. An isolated cell comprising the polynucleotide of claim 1.

9. A pharmaceutical composition comprising the polynucleotide of claim 1 and a pharmaceutically acceptable carrier.

\* \* \* \* \*